US010820992B2

(12) United States Patent
Rajagopal et al.

(10) Patent No.: US 10,820,992 B2
(45) Date of Patent: Nov. 3, 2020

(54) TRANSCATHETER ATRIAL SEALING SKIRT, ANCHOR, AND TETHER AND METHODS OF IMPLANTATION

(71) Applicant: Opus Medical Therapies, LLC, Atlanta, GA (US)

(72) Inventors: Vivek Rajagopal, Atlanta, GA (US); Jaime Eduardo Sarabia, Mableton, GA (US); Yenchin Liao, Cary, NC (US)

(73) Assignee: OPUS MEDICAL THERAPIES, LLC, Atlanta, GA (US)

( * ) Notice: Subject to any disclaimer, the term of this patent is extended or adjusted under 35 U.S.C. 154(b) by 202 days.

(21) Appl. No.: 15/943,971

(22) Filed: Apr. 3, 2018

(65) Prior Publication Data

US 2018/0289474 A1  Oct. 11, 2018

Related U.S. Application Data

(63) Continuation-in-part of application No. 15/943,792, filed on Apr. 3, 2018.
(Continued)

(51) Int. Cl.
*A61F 2/24* (2006.01)

(52) U.S. Cl.
CPC .......... *A61F 2/2418* (2013.01); *A61F 2/2427* (2013.01); *A61F 2220/0016* (2013.01);
(Continued)

(58) Field of Classification Search
CPC ..... A61F 2/24–2466; A61F 2220/0008; A61B 17/0401–2017/0464; A61B 2017/2924; A61B 2017/291
See application file for complete search history.

(56) References Cited

U.S. PATENT DOCUMENTS

| 4,242,715 A | 12/1980 | Laird |
| 4,337,496 A | 6/1982 | Laird |

(Continued)

FOREIGN PATENT DOCUMENTS

| AU | 2016202264 A1 | 11/2016 |
| CA | 3 059 102 A1 | 10/2018 |

(Continued)

OTHER PUBLICATIONS

International Search Report and Written Opinion in corresponding International application No. PCT/US2018/025971 dated Jul. 10, 2018.
(Continued)

*Primary Examiner* — Tan-Uyen T Ho
*Assistant Examiner* — Charles M Wei
(74) *Attorney, Agent, or Firm* — FisherBroyles, LLP; Rachel H. Huffstetler; Rachel Huffstetler

(57) ABSTRACT

A medical assembly implanting an atrial sealing skirt in the heart at an atrial sealing skirt deployment site and related methods of implantation and delivery. An anchor is endovascularly introduced into the heart and implanted to a cardiac wall with an anchor delivery system and delivery cable. A second delivery system introduces a tether which coupled to the implanted anchor and an atrial sealing skirt. The atrial sealing skirt includes a top brim which is positioned to conform to the atrial floor at the deployment site. The sealing skirt may be integrated with a valve or serve as a receptacle.

28 Claims, 24 Drawing Sheets

Related U.S. Application Data

(60) Provisional application No. 62/558,315, filed on Sep. 13, 2017, provisional application No. 62/509,587, filed on May 22, 2017, provisional application No. 62/481,846, filed on Apr. 5, 2017.

(52) U.S. Cl.
CPC .. *A61F 2220/0075* (2013.01); *A61F 2230/005* (2013.01); *A61F 2230/0054* (2013.01); *A61F 2230/0067* (2013.01); *A61F 2250/0004* (2013.01); *A61F 2250/0069* (2013.01)

(56) References Cited

U.S. PATENT DOCUMENTS

| | | |
|---|---|---|
| 4,746,057 A | 5/1988 | Wagner |
| 4,830,360 A | 5/1989 | Carr, Jr. |
| 5,079,776 A | 1/1992 | Crawford |
| 5,312,438 A * | 5/1994 | Johnson ............. A61B 17/0401 606/104 |
| 5,683,451 A * | 11/1997 | Lenker ...................... A61F 2/07 606/198 |
| 5,706,520 A | 1/1998 | Thornton et al. |
| 6,093,162 A | 7/2000 | Fairleigh et al. |
| 7,530,995 B2 | 5/2009 | Quijano et al. |
| 7,780,725 B2 | 8/2010 | Salahieh et al. |
| 8,147,542 B2 * | 4/2012 | Maisano ............. A61B 17/0401 623/2.11 |
| 8,236,049 B2 | 8/2012 | Rowe et al. |
| 8,252,050 B2 * | 8/2012 | Maisano ............. A61B 17/0401 623/2.11 |
| 8,273,973 B2 | 9/2012 | Kimmons et al. |
| 8,333,155 B2 | 12/2012 | Cylvick |
| 8,403,983 B2 | 3/2013 | Quadri et al. |
| 8,449,599 B2 | 5/2013 | Chau |
| 8,489,165 B2 | 7/2013 | Segman |
| 8,545,553 B2 * | 10/2013 | Zipory ............... A61B 17/0401 623/2.37 |
| 8,549,175 B2 | 10/2013 | Krishna |
| 8,690,939 B2 * | 4/2014 | Miller .................... A61F 2/2457 623/2.11 |
| 8,728,155 B2 | 5/2014 | Montorfano et al. |
| 8,790,394 B2 * | 7/2014 | Miller ................. A61B 17/0401 623/2.1 |
| 8,888,843 B2 | 11/2014 | Khairkhahan et al. |
| 8,900,295 B2 * | 12/2014 | Migliazza .......... A61B 17/0401 623/2.19 |
| 8,932,348 B2 | 1/2015 | Solem et al. |
| 8,998,976 B2 | 4/2015 | Gregg et al. |
| 9,005,084 B2 | 4/2015 | Silagy et al. |
| 9,033,383 B2 | 5/2015 | Rampersad |
| 9,034,033 B2 * | 5/2015 | McLean ................. A61F 2/2427 623/2.12 |
| 9,078,749 B2 | 7/2015 | Lutter et al. |
| 9,375,312 B2 | 6/2016 | Weber |
| 9,439,763 B2 | 9/2016 | Geist et al. |
| 9,441,832 B2 | 9/2016 | Bushee |
| 9,474,605 B2 | 10/2016 | Rowe et al. |
| 9,480,559 B2 * | 11/2016 | Vidlund .............. A61L 33/0011 |
| 9,486,306 B2 | 11/2016 | Tegels et al. |
| 9,578,982 B2 | 2/2017 | Rampersad |
| 9,827,092 B2 * | 11/2017 | Vidlund ............. A61B 17/0401 |
| 9,849,001 B2 | 12/2017 | Thompson, Jr. et al. |
| 9,895,221 B2 | 2/2018 | Vidlund |
| 9,986,993 B2 | 6/2018 | Vidlund et al. |
| 10,039,639 B2 | 8/2018 | Marchand et al. |
| 2004/0190383 A1 | 9/2004 | Marcucelli et al. |
| 2005/0137697 A1 * | 6/2005 | Salahieh ................ A61F 2/2418 623/2.11 |
| 2006/0235509 A1 * | 10/2006 | Lafontaine ............ A61F 2/2418 623/2.11 |
| 2006/0241656 A1 | 10/2006 | Starksen et al. |
| 2006/0241745 A1 | 10/2006 | Solem |
| 2007/0118151 A1 * | 5/2007 | Davidson .......... A61B 17/00234 606/144 |
| 2007/0277279 A1 | 12/2007 | Battat |
| 2008/0125860 A1 | 5/2008 | Webler |
| 2009/0276040 A1 * | 11/2009 | Rowe ................... A61B 17/0401 623/2.18 |
| 2010/0016655 A1 * | 1/2010 | Annest ............. A61B 17/00234 600/37 |
| 2011/0004296 A1 * | 1/2011 | Lutter ................. A61B 17/0401 623/1.26 |
| 2012/0078360 A1 | 3/2012 | Rafiee |
| 2012/0136430 A1 | 5/2012 | Sochman et al. |
| 2013/0023985 A1 * | 1/2013 | Khairkhahan ......... A61F 2/2466 623/2.38 |
| 2013/0116780 A1 | 5/2013 | Miller |
| 2013/0172978 A1 * | 7/2013 | Vidlund ............. A61N 17/0401 623/1.12 |
| 2013/0184811 A1 * | 7/2013 | Rowe .................... A61F 2/2418 623/2.11 |
| 2013/0190861 A1 | 7/2013 | Chau et al. |
| 2013/0211508 A1 | 8/2013 | Lane et al. |
| 2013/0304197 A1 | 11/2013 | Buchbinder et al. |
| 2013/0331929 A1 | 12/2013 | Mitra et al. |
| 2014/0005778 A1 | 1/2014 | Buchbinder et al. |
| 2014/0031928 A1 * | 1/2014 | Murphy .............. A61B 17/0057 623/2.18 |
| 2014/0163668 A1 | 6/2014 | Rafiee |
| 2014/0296972 A1 | 10/2014 | Tegels et al. |
| 2014/0316516 A1 | 10/2014 | Vidlund et al. |
| 2014/0379076 A1 | 12/2014 | Vidlund et al. |
| 2015/0142103 A1 | 5/2015 | Vidlund |
| 2015/0250590 A1 | 9/2015 | Gries et al. |
| 2015/0366666 A1 | 12/2015 | Khairkhahan et al. |
| 2016/0022501 A1 | 1/2016 | Schultz et al. |
| 2016/0120646 A1 | 5/2016 | Dwork et al. |
| 2016/0213467 A1 | 7/2016 | Backus et al. |
| 2016/0262878 A1 | 9/2016 | Backus et al. |
| 2016/0262881 A1 * | 9/2016 | Schankereli ......... A61F 2/2436 |
| 2016/0310268 A1 * | 10/2016 | Oba ..................... A61F 2/2436 |
| 2016/0317305 A1 | 11/2016 | Pelled et al. |
| 2016/0324635 A1 | 11/2016 | Vidlund et al. |
| 2016/0367360 A1 | 12/2016 | Cartledge et al. |
| 2017/0143478 A1 | 5/2017 | Schwartz et al. |
| 2017/0172737 A1 | 6/2017 | Kuetting et al. |
| 2017/0209293 A1 | 7/2017 | Combs |
| 2017/0227320 A1 | 8/2017 | Derousse |
| 2017/0312078 A1 | 11/2017 | Krivoruchko |
| 2018/0085215 A1 | 3/2018 | Vaturi et al. |
| 2018/0289473 A1 * | 10/2018 | Rajagopal ............. A61F 2/2427 |
| 2018/0289474 A1 * | 10/2018 | Rajagopal ............. A61F 2/2418 |
| 2018/0289485 A1 * | 10/2018 | Rajagopal ............. A61F 2/2469 |
| 2018/0318071 A1 | 11/2018 | Lozonschi et al. |
| 2019/0015205 A1 * | 1/2019 | Rajagopal ............. A61B 18/00 |
| 2020/0001135 A1 | 1/2020 | Rajagopal |

FOREIGN PATENT DOCUMENTS

| | | |
|---|---|---|
| CA | 3 059 106 A1 | 10/2018 |
| CN | 103826750 A | 5/2014 |
| CN | 105658178 B | 6/2016 |
| CN | 106618798 A1 | 5/2017 |
| DE | 10 2012 002 785 A1 | 8/2013 |
| EP | 1 462 880 A2 | 9/2004 |
| EP | 1 462 880 A3 | 4/2005 |
| EP | 3311774 A1 | 4/2018 |
| KR | 10-2020-0007805 A | 1/2020 |
| KR | 10-2020-0007806 A | 1/2020 |
| UY | 37667 A | 10/2018 |
| UY | 37668 A | 10/2018 |
| WO | 1994/020049 A1 | 9/1994 |
| WO | 2005/094711 A2 | 10/2005 |
| WO | WO2014021905 A1 | 2/2014 |
| WO | 2016050751 A1 | 4/2016 |
| WO | 2016/179427 A1 | 11/2016 |
| WO | 2016186909 A1 | 11/2016 |
| WO | DM/098 100 S | 6/2017 |
| WO | 2017/117560 A1 | 7/2017 |

(56) References Cited

FOREIGN PATENT DOCUMENTS

| WO | 2018/187390 A1 | 10/2018 |
|---|---|---|
| WO | 2018/187495 A1 | 10/2018 |
| WO | 2020/005527 A1 | 1/2020 |

OTHER PUBLICATIONS

International Search Report and Written Opinion in corresponding International application No. PCT/PCT/US2018/026118 dated Jun. 15, 2018.
Toyama et al. Mitral annular motion in patients after transcatheter MitraClip and mitral valve surgery; Echocardiography 2017; 34: 334-339.
Boudjemline Y, Agnoletti G, Bonnet D, et al. Steps toward the percutaneous replacement of atrioventricular valves an experimental study. Journal of the American College of Cardiology 2005;46:360-5.
Bai Y, Chen HY, Zong GJ, et al. Percutaneous establishment of tricuspid regurgitation: an experimental model for transcatheter tricuspid valve replacement. Chinese medical journal 2010;123:806-9.
Laule M, Stangl V, Sanad W, Lembcke A, Baumann G, Stangl K. Percutaneous transfemoral management of severe secondary tricuspid regurgitation with Edwards Sapien XT bioprosthesis: first-in-man experience. Journal of the American College of Cardiology 2013;61:1929-31.
Lauten A, Doenst T, Hamadanchi A, Franz M, Figulla HR. Percutaneous bicaval valve implantation for transcatheter treatment of tricuspid regurgitation: clinical observations and 12-month follow-up. Circulation Cardiovascular interventions 2014;7:268-72.
Lauten A, Ferrari M, Hekmat K, et al. Heterotopic transcatheter tricuspid valve implantation: first-in-man application of a novel approach to tricuspid regurgitation. European heart journal 2011;32:1207-13.
Lauten A, Figulla HR, Unbehaun A, et al. Interventional Treatment of Severe Tricuspid Regurgitation: Early Clinical Experience in a Multicenter, Observational, First-in-Man Study. Circulation Cardiovascular interventions 2018;11:e006061.
Lauten A, Figulla HR, Willich C, et al. Percutaneous caval stent valve implantation: investigation of an interventional approach for treatment of tricuspid regurgitation. European heart journal 2010;31:1274-81.
Lauten A, Laube A, Schubert H, et al. Transcatheter treatment of tricuspid regurgitation by caval valve implantation-experimental evaluation of decellularized tissue valves in central venous position. Catheterization and cardiovascular interventions : official journal of the Society for Cardiac Angiography & Interventions 2014.
Figulla HR, Kiss K, Lauten A. Transcatheter interventions for tricuspid regurgitation—heterotopic technology: TricValve. EuroIntervention : journal of EuroPCR in collaboration with the Working Group on Interventional Cardiology of the European Society of Cardiology 2016;12:Y116-8.

Barbanti M, Ye J, Pasupati S, Ei-Gamel A, Webb JG. The Helio transcatheter aortic dock for patients with aortic regurgitation. EuroIntervention : journal of EuroPCR in collaboration with the Working Group on Interventional Cardiology of the European Society of Cardiology 2013;9 Suppl:S91-4.
Hahn RT, Meduri CU, Davidson CJ, et al. Early Feasibility Study of a Transcatheter Tricuspid Valve Annuloplasty: SCOUT Trial 30-Day Results. Journal of the American College of Cardiology 2017;69:1795-806.
Rosser BA, Taramasso M, Maisano F. Transcatheter interventions for tricuspid regurgitation: TriCinch (4Tech). EuroIntervention : journal of EuroPCR in collaboration with the Working Group on Interventional Cardiology of the European Society of Cardiology 2016;12:Y110-2.
Stephan von Bardeleben R, Tamm A, Emrich T, Munzel T, Schulz E. Percutaneous transvenous direct annuloplasty of a human tricuspid valve using the Valtech Cardioband. European heart journal 2017;38:690.
Kuwata S, Taramasso M, Nietlispach F, Maisano F. Transcatheter tricuspid valve repair toward a surgical standard: first-in-man report of direct annuloplasty with a cardioband device to treat severe functional tricuspid regurgitation. European heart journal 2017.
Rogers J. Transcatheter TR solution 6: Millipede. Transcatheter Cardiovascular Therapeutics; 2017 Nov. 1, 2017; Denver, Colorado.
Parada-Campelo F, Perlman G, Philippon F, et al. First-in-Man Experience of a Novel Transcatheter Repair System for Treating Severe Tricuspid Regurgitation Journal of the American College of Cardiology 2015;66:2475-83.
Nickenig G, Kowalski M, Hausleiter J, et al. Transcatheter Treatment of Severe Tricuspid Regurgitation With the Edge-to-Edge MitraClip Technique. Circulation 2017;135:1802-14.
Cao P. Catheter-Based Tricuspid Valve Replacement Via Right Atrium: An Animal Experimental Study. Transcatheter Cardiovascular Therapeutics; 2017; Denver, Colorado.
Navia JL, Kapadia S, Elgharably H, et al. First-in-Human Implantations of the NaviGate Bioprosthesis in a Severely Dilated Tricuspid Annulus and in a Failed Tricuspid Annuloplasty Ring. Circulation Cardiovascular interventions 2017;10.
Regueiro, et al. Transcatheter Mitral Valve Replacement: Insights From Early Clinical Experience and Future Challenges; JACC vol. 69, No. 17, 2017; May 2, 2017: 2175-92.
Non-Final Office Action received for U.S. Appl. No. 15/943,792 dated Jan. 8, 2020, 50 pages.
International Search Report and Written Opinion of the International Searching Authority dated Aug. 30, 2019, in International Application No. PCT/US19/36428.
International Search Report and Written Opinion issued in corresponding International Application No. PCT/US2019/057145 dated Dec. 31, 2019.
International Preliminary Report on Patentability received for PCT Application Serial No. PCT/US2018/025971 dated Oct. 17, 2019, 9 pages.
International Preliminary Report on Patentability received for PCT Application Serial No. PCT/US2018/026118 dated Oct. 17, 2019, 11 pages.

* cited by examiner

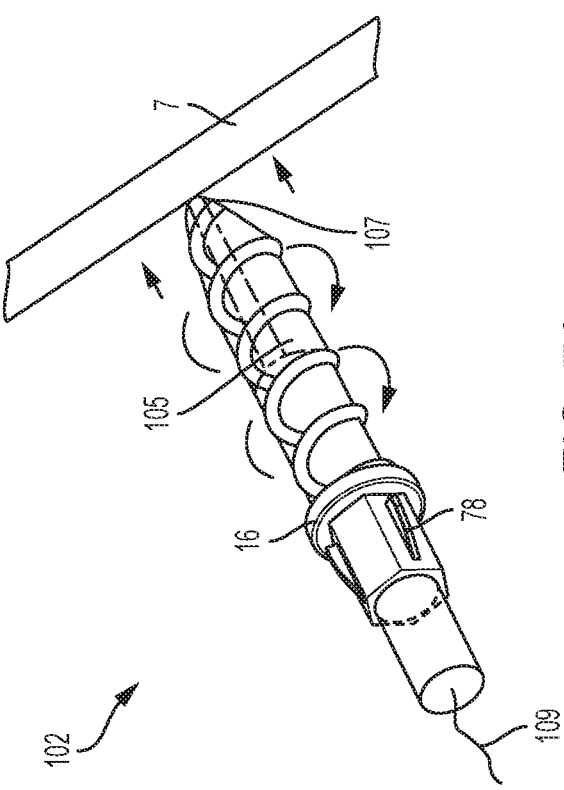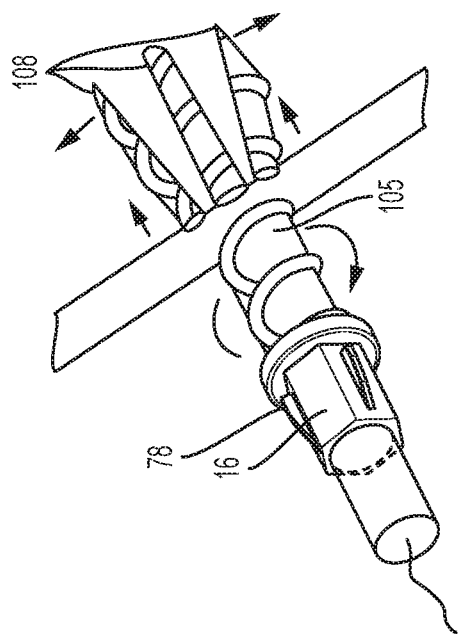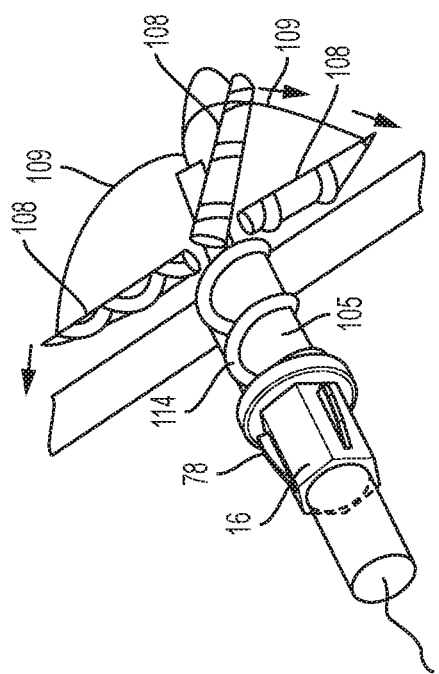

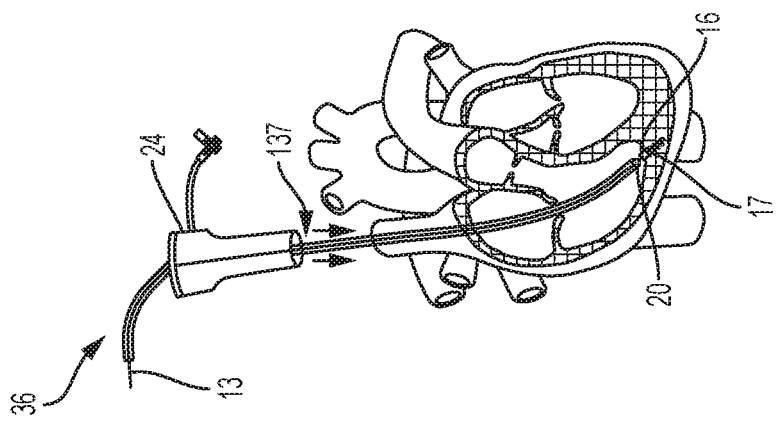
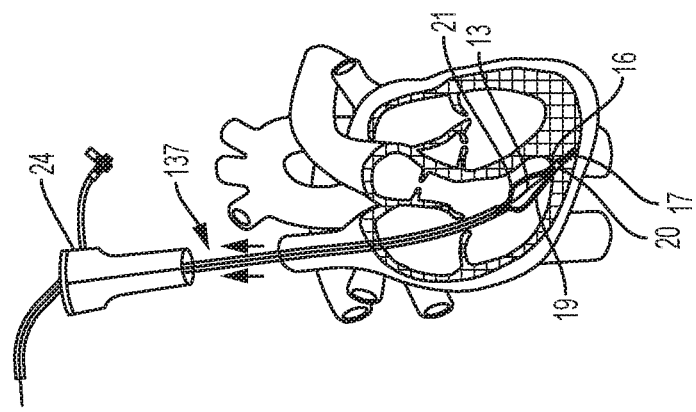
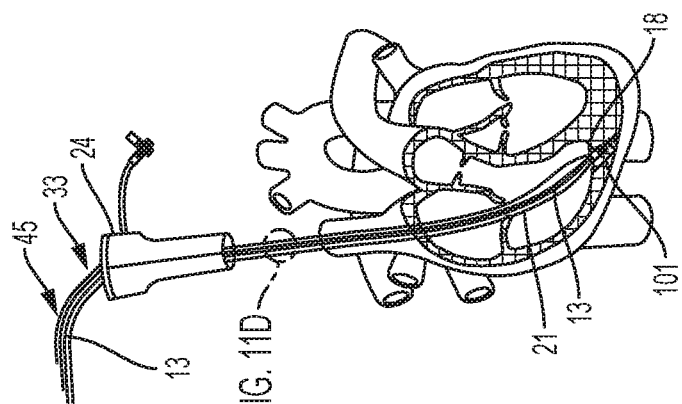
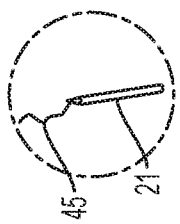

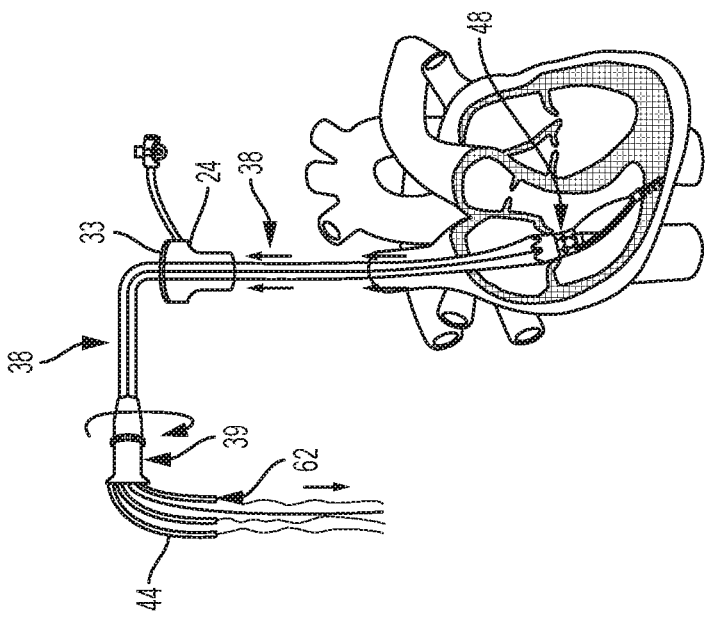
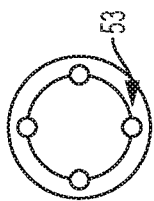
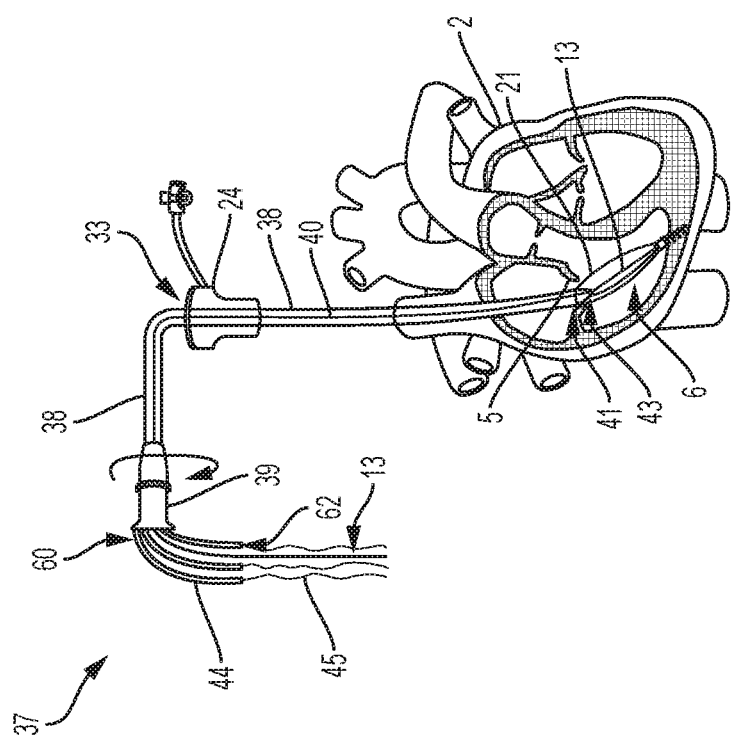
FIG. 12B
FIG. 12C
FIG. 12A

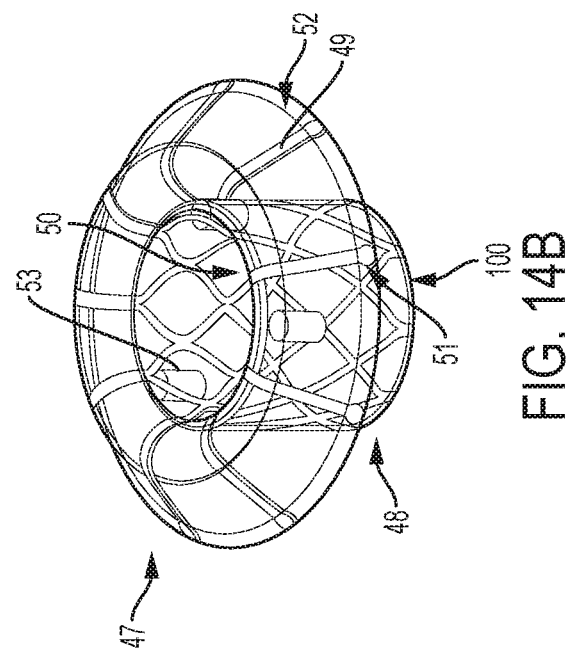
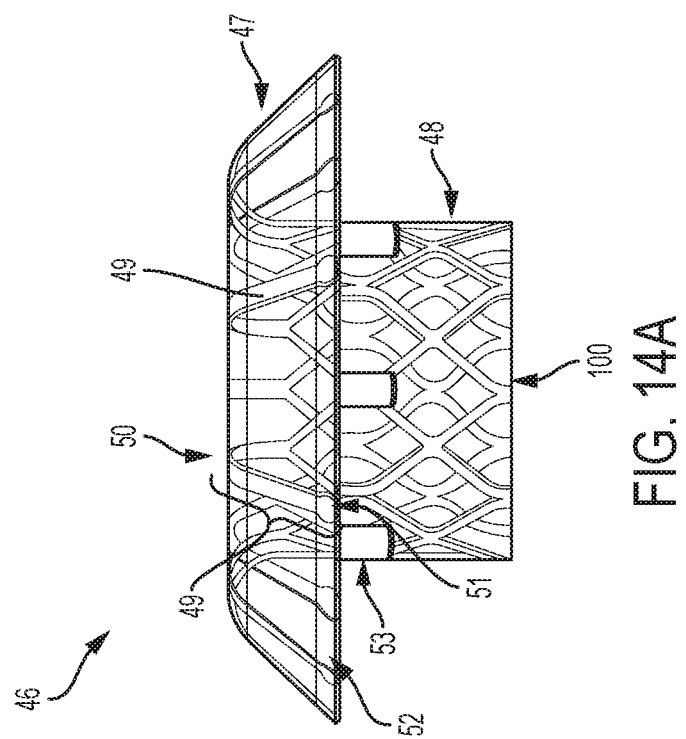
FIG. 14B
FIG. 14A

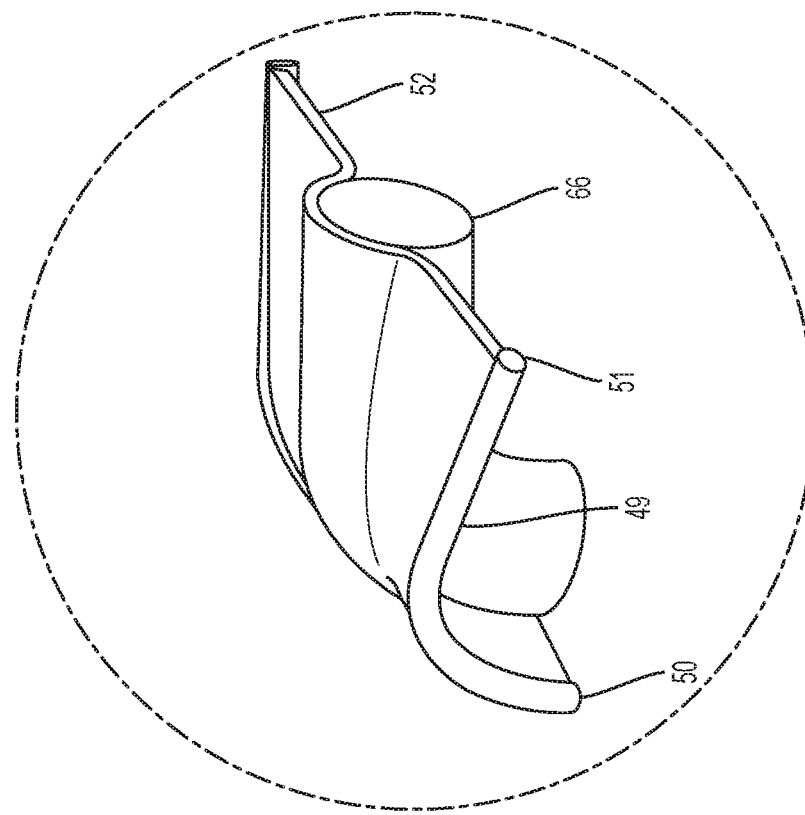
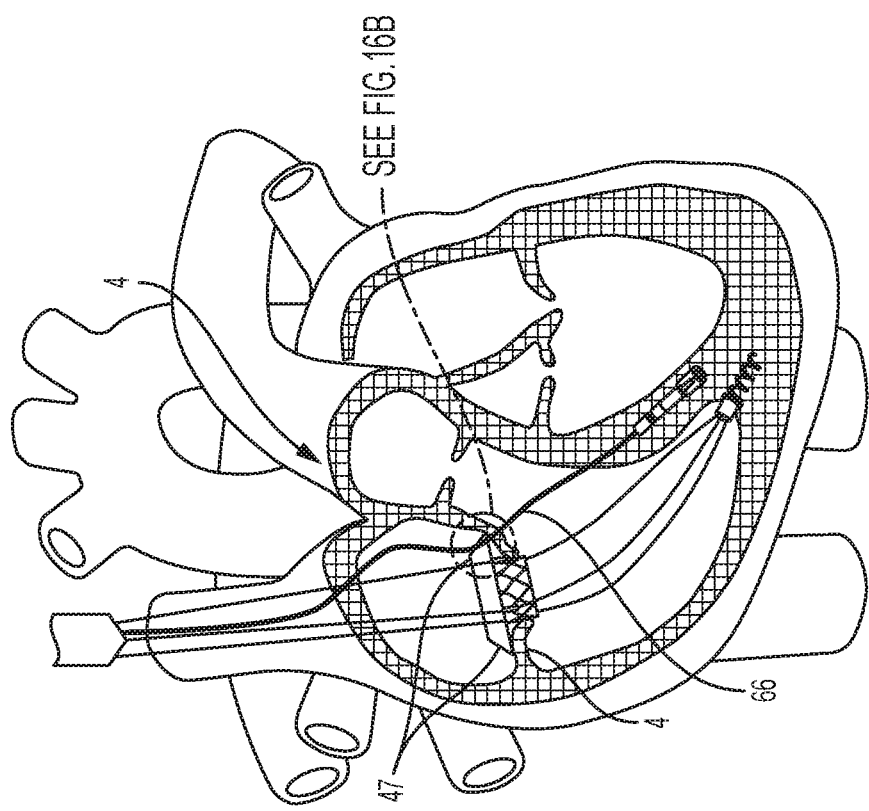
FIG. 16B
FIG. 16A

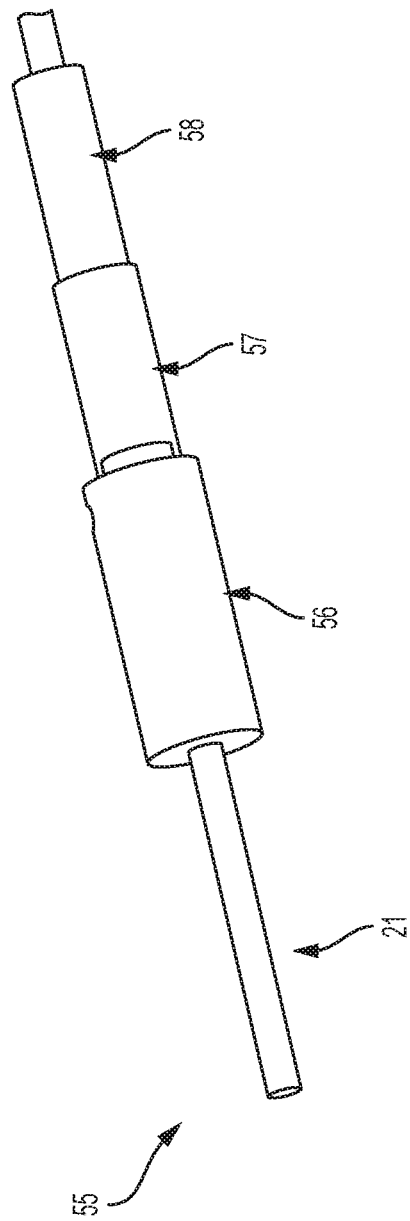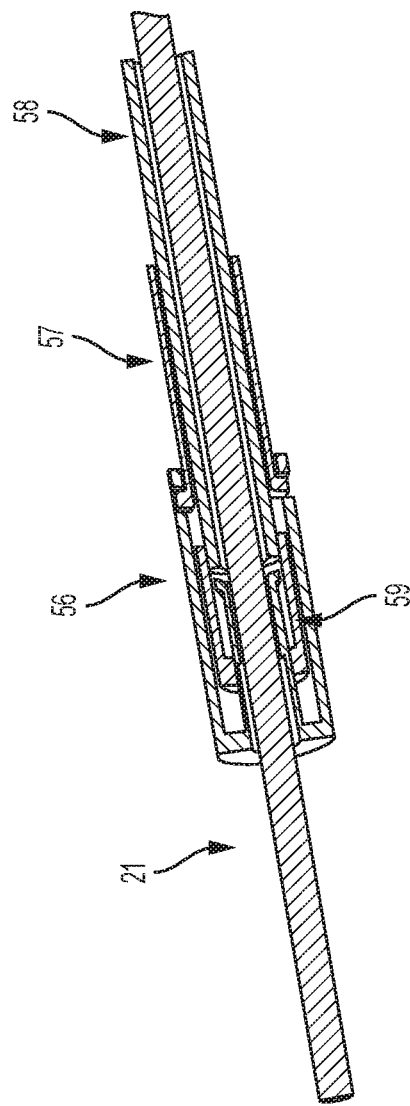
FIG. 18A
FIG. 18B

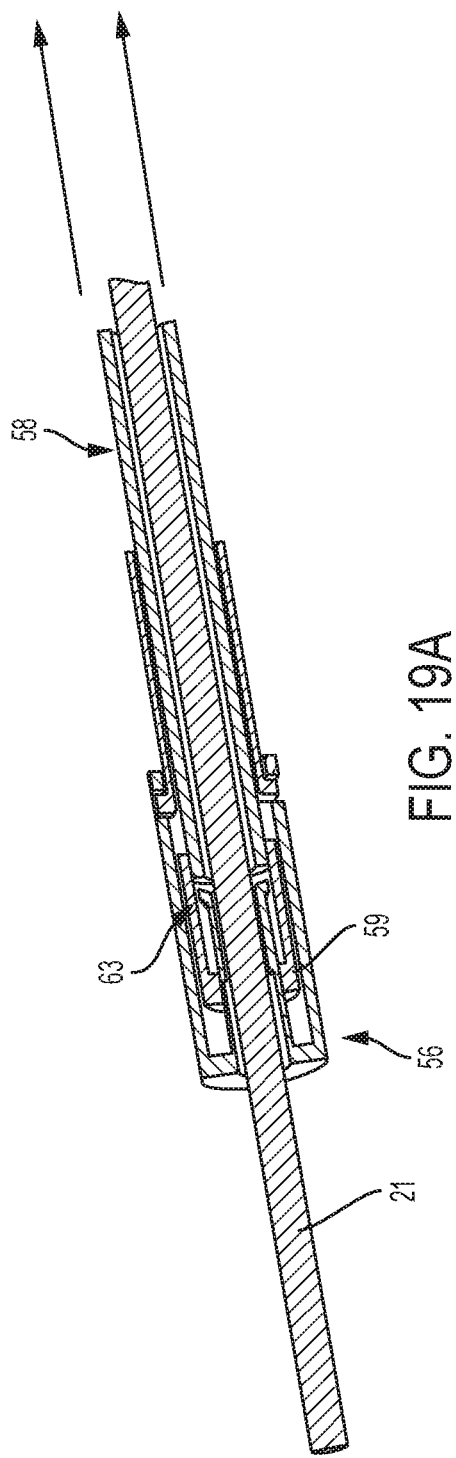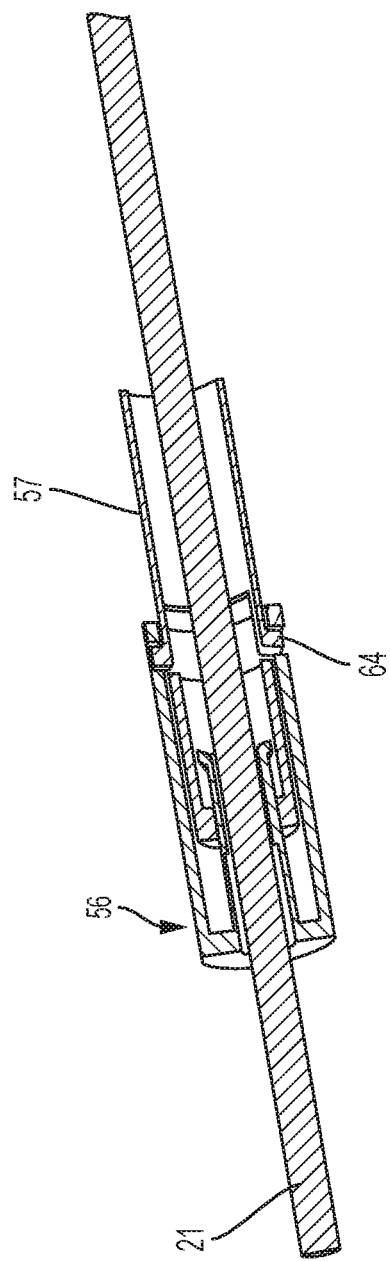

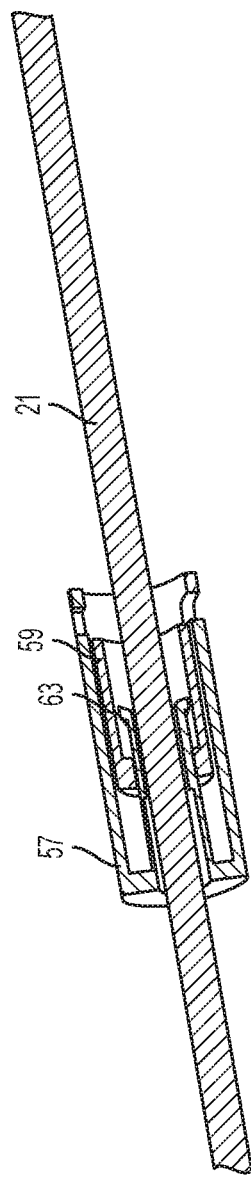
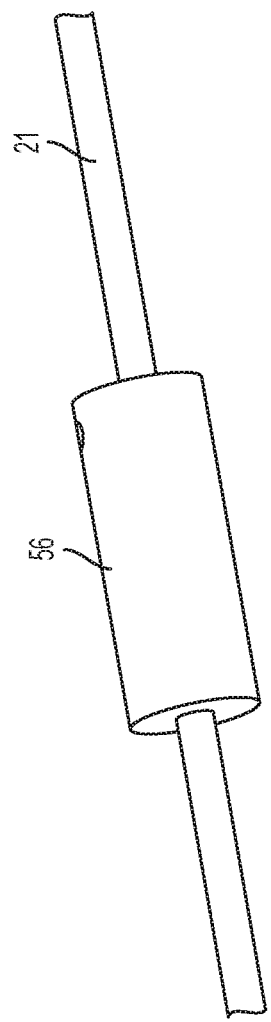
FIG. 20A
FIG. 20B

TRANSCATHETER ATRIAL SEALING SKIRT, ANCHOR, AND TETHER AND METHODS OF IMPLANTATION

CROSS REFERENCE TO RELATED APPLICATIONS

The application is a continuation-in-part and claims priority to U.S. patent application Ser. No. 15/943,792 (filed Apr. 3, 2018) and which claims the benefit of and priority to Provisional Patent Application Ser. Nos. 62/481,846 (filed Apr. 5, 2017), 62/509,587 (filed May 22, 2017), and 62/558,315 (filed Sep. 13, 2017), the disclosures of all are herein incorporated by reference.

FIELD OF THE INVENTION

The present invention relates generally to medical devices and systems that are implanted minimally invasively in the heart and methods of implantation of these devices and systems. More specifically, the invention pertains to medical devices and systems that are implanted minimally invasively into any wall of the heart, using one or more anchors that tether transcatheter valves or other cardiac devices inside the heart. The invention also pertains to an atrial skirt sealing transcatheter valves to reduce paravalvular regurgitation, with or without the presence of intracardiac leads.

BACKGROUND OF THE INVENTION

Transcatheter valves have proven safe and effective for the replacement of native cardiac valves. These valves have been tested extensively for replacement of aortic, mitral, and pulmonic valves, but replacement of tricuspid valves remains challenging given the complex and delicate anatomy to which prostheses must attach. Anchoring transcatheter valves, in general, or transcatheter tricuspid valves, in particular, remains difficult, because doing so, either in the in-situ position of cardiac valves, or in other body lumens, requires interaction with a great variety of shapes and sizes of either cardiac valve annuli or other lumens. In this regard, the ability to tether transcatheter valves with one or more anchors affixed to intracardiac wall(s) would give greater security and flexibility for the transcatheter prosthesis by lessening need for fixation at the exact site of the prosthesis. This would be particularly advantageous for the anchoring of a transcatheter tricuspid valve prosthesis.

Several groups have described intracardiac anchors and tethers, but these systems have limitations in their applications. For example, Vidlund (1) and Lutter (2) describe a system of anchoring a prosthetic valve using a single tether connecting the valves distal end to an "epicardial tether securing device" (Vidlund patent), which could also be described as an anchor. Because the securing device is located outside the heart's apex (epicardial), this system requires accessing the apex of the heart via the chest wall. The need to access the heart via the chest might increase the risk of the procedure in patients with a decreased pumping function (ejection fraction), or in patients with fragile tissues, particularly in applications involving the tricuspid valve.

In contrast, Rowe and colleagues (3) describe a coaptation device for tricuspid regurgitation that is anchored to the right ventricular apex using an endovascular approach without the need to access the heart via the chest wall. Rowe states: "A flexible anchor rail connects to the anchor and a coaptation element on a catheter rides over the anchor rail. Finally, there is a proximal anchoring feature to fix the proximal end of the coaptation catheter subcutaneously adjacent the subclavian vein." The first limitation of this application is the inability to retrieve and reposition the anchor in the case of a wrong site or sub-optimal deployment. The next limitation is that the anchor rail is fixed to the anchor. In contrast to this, it would be advantageous to be able to deploy the anchor first, followed by delivery of a cable or tether of varying diameter or material that locks into the anchor. By making the tether independent of the anchor, multiple permutations of tether/anchor elements can be deployed easily, maximizing the ability to customize the application depending on the specific clinical need. Finally, this application describes a fixed connection between the anchor, distal anchor rail, coaptation device, and proximal anchor rail, which requires a large amount of anchor rail to remain in the superior vena cava and innominate/subclavian veins. The proximal anchor rail is connected to a subcutaneous pocket, and all of this brings the attendant risks of permanent venous leads, specifically thrombosis, infection, and venous stenosis.

Solem and colleagues (4) get around some of these limitations with their application, which describes the possibility of a two-stage process whereby the anchor can be deployed first, followed by connecting an "elongate body portion" to the anchor, with the elongate body portion connecting to tethers and the blood flow controlling apparatus. Having a two-stage process could be useful "for situations where a user desires to replace a canopy or other portion of the device . . . if . . . the expandable valve portion is not of the optimal size or not at an optimal distance from the anchor." The anchor may consist of "arms or hooks that expand outward as the anchor portion . . . is exposed." The elongate body can connect to the anchor via multiple mechanisms, including "snap-type or quick-connect connections". In one embodiment, the elongate body can have a "ring-like structure . . . configured to advance around . . . the anchor generally tubular projection". To facilitate connection, the "anchor proximal end . . . includes a coupling member . . . in the form of a generally tubular projection . . . having outwardly extending locking clips . . . that can be bent inwardly in response to inward pressure . . . but will snap back outward once the inward pressure is released."

Despite some of the advantages of Solem's application, this application also suffers limitations. First, the preferred method of delivering the anchor is by advancing the anchor delivery catheter via a chest wall incision, then into an incision through one of the chambers of the heart. It would be even more desirable to be able to deliver the anchor via a true endovascular approach (e.g. via the internal jugular or femoral veins) without the need for chest and cardiac cavity incisions. Next, the anchor consists of expandable arms or hooks that dig into the cardiac wall, then flex backwards, analogous to fish hooks. Solem contends that the expandable hooks of the anchor can be retrieved: "As the anchor portion . . . is drawn back into the distal end sheath . . . inward pressure on the prongs . . . from the distal end sheath . . . will cause the prongs . . . of the anchor portion . . . to collapse inwardly . . . thereby collapsing anchor portion . . . back to its delivery (i.e. predeployment) condition . . . " It is doubtful, however, that the tissue-engaging, backward-bending prongs can be retrieved easily in this fashion without damaging tissue in the process, and a more safely retrievable anchor is desired. Further, the prongs might be safe in one location of the heart, but might cause damage (i.e. perforation) if they need to be moved to a different location, because the arm length is not adjustable.

Therefore, the ability to change tissue depth of the anchor (e.g. the interventricular septum can tolerate a greater depth compared to ventricular free wall) is desirable. Next, the connection of the elongate member to the anchor, even if via a separate step, is fixed, so that the elongate member cannot rotate around the axis of the anchor. When adjusting a transcatheter valve on the elongate member, it might be necessary to rotate the valve to seat better in the native cardiac annulus, and Solem's elongate member, once fixed to the anchor, cannot rotate. Finally, Solem's application requires that the tethers are connected to the anchor via the elongate member. It would be particularly advantageous to be able to connect the tethers directly to the anchor, with the ability for the tethers to rotate about the axis of the anchor, because this would most closely mimic the function of chordae tendinae (the heart's natural tethers), which connect directly from cardiac walls to cardiac valves.

Moreover, limiting paravalvular regurgitation of transcatheter mitral and tricuspid valves is challenging because the mitral and tricuspid annuli are complex saddle-shaped structures that are highly dynamic during the cardiac cycle. Compounding this difficulty for the tricuspid valve is the frequent presence of intracardiac leads in patients with significant tricuspid regurgitation (TR). Because ventricular leads traverse the annulus from the right atrium to the right ventricle, a transcatheter tricuspid valve must seal around both the annulus and the lead to limit regurgitation in these patients.

In patients receiving transcatheter aortic valve replacements (TAVR), investigators have developed technologies to mitigate paravalvular regurgitation, but these approaches have limitations, especially in the presence of intracardiac leads. In particular, balloon-expandable, mechanically-expandable, and self-expanding TAVRs have incorporated sealing membranes around their stent frames at the annular level to lessen paravalvular regurgitation. The sealing membranes consist either of polyethylene terephthalate, known as PET or Dacron, or of a porcine pericardial tissue wrap. These sealing membranes work by filling in the interstices between the outside of the TAVR and the aortic annulus, but this requires direct apposition of the valve against the annulus. For transcatheter tricuspid valves, direct apposition of the valve frame to the tricuspid annulus might not be desirable or feasible because unlike the aortic annulus, the tricuspid annulus is distensible, with minimal external support, and prone to injury. Additionally, sealing an intracardiac lead by trapping it between the valve frame and annulus would increase the risk of injury to the lead, which is undesirable.

Most transcatheter mitral valve replacements (TMVR) already use a similar mechanism to limit paravalvular regurgitation by trapping the base of the mitral leaflets between the valve frame and annulus. Thus, like the TAVR approach, the TMVR approach to lessen paravalvular regurgitation could damage the fragile tricuspid annulus, or damage intracardiac leads by trapping them between the valve frame and annulus. For example, the Medtronic Intrepid and NSCI Navigate valves anchor by either radial force against the annulus (Intrepid) or via annular "winglets" or hooks (Navigate). The CardiAQ-Edwards TMVR interacts directly with the annulus using a sub-annular clamping mechanism, while the Neovasc Tiara valve interacts indirectly via the fibrous trigones and also uses native leaflet engagement (both mechanisms could trap and injure leads). Three TMVR devices—Caisson, HighLife, and MValve—use an annular anchor as a docking system for the TMVR device, which would squeeze, and likely damage, any intracardiac lead between the anchor and the TMVR device.

Damage to intracardiac leads is not the only concern about the way TMVR devices mitigate paravalvular regurgitation. Because most TMVR devices reduce regurgitation by sealing the mitral annulus via direct anchoring to the annulus, these devices constrain, to varying degrees, freedom of mitral annular motion. Constraining this freedom might contribute to left ventricular dysfunction. For example, a study comparing transcatheter mitral valve repair (using Abbott Vascular's MitraClip device) to open heart surgery showed that mitral annular motion was significantly lower with open heart surgery, which the authors suggested was a factor in the lower left ventricular ejection fraction (LVEF) after open heart surgery compared to transcatheter repair. Similarly, a study comparing flexible to rigid mitral annuloplasty rings found a significantly lower LVEF with rigid rings, which constrain mitral annular motion more than flexible rings. Thus, in order to limit paravalvular regurgitation, current TMVR devices must anchor and constrain the mitral annulus, and this could have deleterious effects on left ventricular function.

To limit paravalvular regurgitation while avoiding constraint of the mitral annulus, the TMVR atrial skirts, by themselves, might lessen paravalvular regurgitation and seal around intracardiac leads; for example, the Medtronic Intrepid, Neovasc Tiara, and the Highlife TMVR devices have atrial skirts that lessen paravalvular regurgitation, and could facilitate sealing around intracardiac leads; however, without mitral annular anchoring used by these TMVR devices, all of these skirts suffer important limitations. The Neovasc Tiara atrial skirt suffers the biggest limitation by being asymmetrical to conform to the "D-shaped" mitral annulus and to the aorto-mitral curtain. This asymmetry is incompatible with the right atrial floor and tricuspid annulus. The skirts of the other TMVRs are symmetrical and are potentially compatible with the right atrial floor and tricuspid annulus, but these skirts lack the downward force and flexibility (along the perpendicular axis of the annulus) that are required for either reduction of paravalvular regurgitation or for sealing of intracardiac leads. Although Abbott Vascular Tendyne valve avoids annular anchoring by using an epicardial valve tether, its skirt also lacks the force and flexibility to seal around an intracardiac lead. The Tendyne valve skirt, like the skirts of other TMVR devices, consists of flexible interconnected wire loops covered with PET, and all these skirts assume a funnel shape with the wide top in the atrium and the narrow bottom at the valve annulus. These funnel-shaped skirts easily flex inwards and do not have any mechanism to increase outward and downward force of the atrial skirt differentially. For example, a mechanism to increase these forces in the skirt where it interacts with the lead would allow the skirt to control and constrain the lead. The aforementioned atrial skirts do not have such a mechanism; therefore, a lead traversing the right atrium into the ventricle would not be constrained by the top of the skirt; instead, the lead would likely bow the skirt inward, creating a discontinuity of the skirt at the atrial floor, allowing paravalvular regurgitation.

Finally, another limitation of current atrial skirts is their fixation to their associated TMVR devices. It would be advantageous to be able to uncouple the atrial skirt from the valve; that is, to have the ability to place an atrial skirt first, followed by deployment of a transcatheter valve in the mitral or tricuspid space. Doing this would allow many combinations of atrial skirts and valves, which would maximize the ability to customize transcatheter valve placement and sealing depending on atrial, annular, and ventricular variations in anatomy.

Therefore, it is highly desirable to create a transcatheter valve skirt with several distinct features. One, its efficacy should be independent of mitral or tricuspid annular anchoring to avoid injuring annular anatomy or impairing ventricular function. Second, the skirt should be able to bend downwards with differential flexibility and force to conform to the local topography of the atrial floor, and to conform and seal around intracardiac leads. Finally, it would be advantageous to develop an atrial skirt that could be placed either as an integrated part of the transcatheter valve or independently of the transcatheter valve to facilitate the docking and sealing of pre-existing transcatheter valves to either the mitral or tricuspid annulus. Creating a skirt than can be independently placed and used as a docking system significantly expands the possibilities for treating patients suffering from mitral or tricuspid disease.

Applicants' Ser. No. 15/943,792 discloses a Transcatheter Anchor and Tether Devices, Systems and Methods of Implantation including an anchor delivery system for introducing a tether coupled to the anchor and a valve delivery system for delivering, positioning and sealing the valve. According to the below described disclosure, the anchor delivery system comprises an anchor which is implanted and not initially coupled to a tether.

SUMMARY OF THE INVENTION

Presented herein are medical devices and systems that are implanted minimally invasively for the implantation of one or more anchors into cardiac walls for the purpose of connecting tethers from the anchor to intracardiac devices, in particular transcatheter valves. Additionally, presented are medical devices and systems which are implanted minimally invasively for the sealing of transcatheter valves to reduce paravalvular regurgitation, with or without the presence of intracardiac leads. In one aspect, the anchor is delivered completely endovascularly, using an anchor delivery catheter, without the need for chest or cardiac incisions.

In one aspect, the system comprises an anchor introducer sheath, an anchor delivery catheter, and an anchor screw attached to an anchor cap configured to accept a tether. The tether is configured to attach to one or more cords, and the tether attaches to the intracardiac device via the cords, such as a transcatheter valve and the like.

According to various aspects, the anchor screw may be an inclined plane wrapped around a nail-like head, or the anchor screw may be any helical device, such as an Archimedes-type screw, and may be "right-handed" or "left-handed". The anchor screw is composed of any metal alloy, such as, but not limited to, nitinol, stainless steel, titanium, or cobalt-chromium.

The anchor cap, is also be composed of any metal alloy, and is coupled to a proximal portion of the anchor screw. A proximal end of the anchor cap defines an internal "female" thread, which accepts "male" threads of a distal end of a delivery cable. In one aspect, the delivery cable remains attached to the anchor cap during fixation of the anchor cap to the cardiac wall, which occurs by rotation of anchor cap, thereby driving the anchor screw into the cardiac wall. In another aspect, after fixation of the anchor to the wall, the delivery cable is used to guide the tether until the docking ring of the tether couples with the anchor. Finally, the delivery cable may be unscrewed from the anchor cap and removed.

In one aspect, the tether has a docking ring attached to at least one docking ring arm with an eyelet defined at the proximal end of the docking ring arm. Each eyelet connects to a distal end of a tether rod that attaches to the eyelet via a hook. The tether rod is composed of any metal alloy, and a proximal end of the tether rod is coupled to a cord. In one aspect, the docking ring of the tether is advanced over the anchor cap, depressing the protruding locking arms of the anchor cap. In another aspect, the docking ring reaches the end of the anchor cap, allowing the protruding locking arms to push out, thereby locking the docking ring, and therefore the tether, in place. In another aspect, even after being locked into place, the tether is free to rotate about the longitudinal axis of the anchor cap, without affecting the position of the anchor cap or the anchor screw. For retrieval, the anchor delivery catheter reverts over the locking arms, thereby depressing them, and allowing the docking ring of the tether to be retracted. According to one aspect, the atrial sealing skirt is integrated with a transcatheter valve, and is delivered completely endovascularly, without the need for chest or cardiac incisions. Alternatively, the atrial sealing skirt is independent of the transcatheter valve and is delivered completely endovascularly, without the need for chest or cardiac incisions. By being placed independently of the transcatheter valve, the atrial skirt serves as a docking system for any transcatheter valve.

In one aspect, whether or not the atrial skirt is integrated with the valve, the system comprises an atrial sealing skirt configured to secure to the atrial floor and at least one tether configured to couple and/or secure the atrial sealing skirt to any intracardiac wall via the tether's interaction with an anchor.

In one aspect, the atrial sealing skirt is self-expanding and composed of nitinol and covered with either synthetic materials such as, but not limited to, polytetrafluoroethylene (PTFE) or polyethylene terephthalate (PET), or biological membranes such as, but not limited to, bovine or porcine pericardial tissue.

In one aspect, the membrane covering the atrial skirt has a diameter greater than the annulus at the site of apposition so that in use the membrane substantially covers the mitral or tricuspid annulus.

The frame of the atrial skirt begins as a cylindrical shape, with the bottom of the cylinder at or below the valve annular level, and with the top of the cylinder extending into the atrium. From the top of the cylinder extends a top brim, composed of one or more wire extensions, made of laser-cut or formed nitinol. These extensions are fashioned as shapes such as, but not limited to, lines, arcs, hooks, circles, ellipses, sinusoidal curves, or of polygons of three or more sides. The extensions of the top brim, like the body of the skirt, are covered and/or connected with synthetic or biological membranes. The top brim is perpendicular to the atrial skirt body, or may bend toward the atrial floor as either as a convex or concave curve. To facilitate sealing as the top brim bends toward the atrial floor, the covering fabric consists of either a braided or knit fabric, which allows for "stretchability", improving the ability to conform to the topography of the atrial floor and wrap around any intracardiac leads.

In one aspect, adjacent to the top brim, running longitudinally along the interior or exterior of skirt body, are one or more conduits, which take the shape of a cylinder whose cross-section is any portion of a circle, ellipse, parabola, or hyperbola, or take the shape of a polyhedron with a flat base and top which assume the shape of a polygon with three or more sides. These conduits are constructed from the membrane covering the skirt, or may be made of, but not limited to, stainless steel, nitinol or other metal alloys. The one or more conduits are hollow and accommodate at least one cord attached to at least one tether, and each conduit attaches to a detachable lock near the atrial surface of the skirt.

The at least one anchoring system comprises an anchor screw configured to be screwed into or otherwise securely attached to any intracardiac wall. In one aspect, a tether is coupled to the anchor screw via the anchor cap, and at least one cord extends from the tether through the at least one conduit of the skirt body. Thus, the sealing skirt is threaded onto the cord via the conduit so that the sealing skirt, independently or integrated to a valve, slidingly interacts with the cord. In another aspect, the proximal end of the cord attaches to a suture, which extends outside of the heart to be accessible by a user.

The system further comprises at least one atrial positioning rod whose proximal end is attached to the delivery system, and whose distal end is reversibly coupled to a detachable lock, which is attached to the proximal end of the conduit of the atrial skirt. Through the inner lumen of the positioning rod runs suture and/or cord, so that the positioning rod pushes or pulls the atrial skirt, thereby applying differential force and flexion to the associated top brim, allowing apposition to the atrial floor and/or conformation around an intracardiac lead. In another aspect, rotation of the positioning rod and/or pushing or pulling of internal elements of the positioning rod causes the detachable lock to engage the cord and/or suture, securing the cord and/or suture to the atrial skirt, maintaining the force and flexion of the atrial skirt to atrial floor and/or intracardiac lead.

Related methods of operation are also provided. Other apparatuses, methods, systems, features, and advantages of the medical devices and systems that are implanted minimally invasively in the heart will be or become apparent to one with skill in the art upon examination of the following figures and detailed description. It is intended that all such additional apparatuses, methods, systems, features, and advantages be included within this description, be within the scope of the medical devices and systems that are implanted minimally invasively in the heart, and be protected by the accompanying claims.

BRIEF DESCRIPTION OF THE DRAWINGS

FIG. 7A-7C are perspective views of an anchor according to an alternative aspect with a splitting anchor screw;

FIG. 11A is a perspective view of the tether delivery assembly onto the implanted anchor;

FIGS. 11B and 11C are a perspective view of the tether delivery assembly being removed;

FIG. 11D is an enlarged view of the fusion of the cord with the suture;

FIG. 12A is a perspective view of the sealing skirt delivery device wherein the atrial sealing skirt delivery system is positioned in the right ventricle;

FIG. 12B is a perspective view of the atrial sealing skirt delivery device wherein the delivery guide is partially withdrawn and the sealing skirt is expanded;

FIG. 12C is an end view of the atrial sealing skirt;

FIGS. 14A and 14B are side elevational view and top perspective view of the atrial sealing skirt;

FIG. 16A is a cut-away perspective view of the heart showing the atrial sealing skirt conforming to the atrial floor and sealing around an intracardiac lead;

FIG. 16B is an enlarged perspective view of the atrial skirt conforming to and sealing around an intracardiac lead;

FIG. 18A is a perspective view of the locking system;

FIG. 18B is a perspective cut-away view of the locking system;

FIG. 19A is a cross-sectional side view of the locking system for atrial sealing skirt positioning in an un-locked position;

FIG. 19B is a cross-sectional side view of the locking system for atrial sealing skirt positioning in a locked position;

FIG. 20A is a partially cut away view of the locking system in the locked position;

FIG. 20B is a perspective view of the locking system;

DETAILED DESCRIPTION OF THE INVENTION

Figure 1:
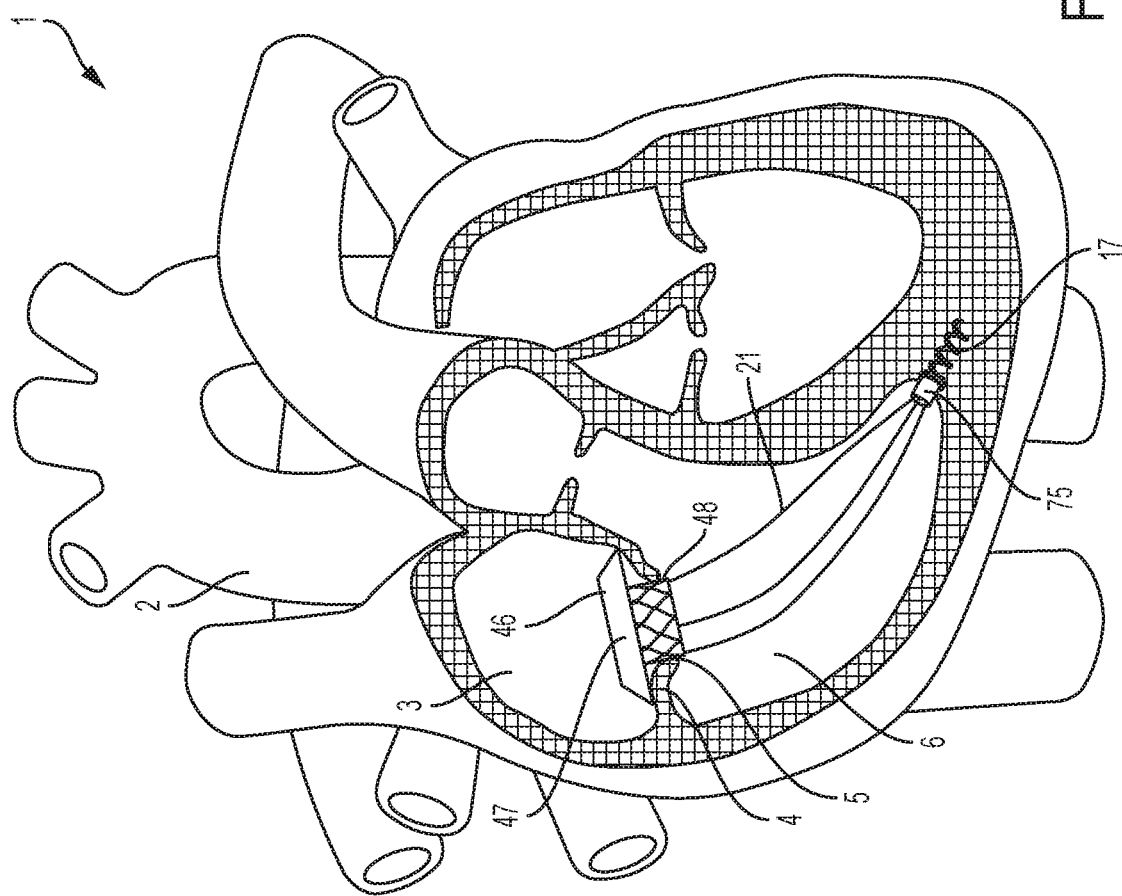
FIG. 1 is a cut-away perspective view of a heart showing the transcatheter atrial sealing skirt system positioned across the tricuspid valve in the heart.

The present invention can be understood more readily by reference to the following detailed description, examples, and claims, and their previous and following description. Before the present system, devices, and/or methods are disclosed and described, it is to be understood that this invention is not limited to the specific systems, devices, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known aspect. Those skilled in the relevant art will recognize that many changes can be made to the aspects described, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used herein, the singular forms "a," "an" and "the" include plural referents unless the context clearly dictates otherwise. Thus, for example, reference to a "tether" includes aspects having two or more tethers unless the context clearly indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not. As used herein "fluid" refers to any substance that is free to flow and include liquids, gases, and plasma. "Fluid communication" as used herein refers to any connection or relative positioning permitting substances to freely flow between the relevant components.

The application relates to medical devices and systems to be minimally invasively implanted in the heart and methods of implantation of these devices and systems. More specifically, the application relates to devices, methods and systems for endovascularly introducing and anchoring an anchor 75 to a cardiac wall and implanting a valve 100 (see FIGS. 23 and 14A and 14B) in the heart tethered to the anchor 75 to replace the native valve. Also, a tethering assembly cooperates with the anchor 75 connecting the valve 100 to the anchor 75. Furthermore, the valve 100 includes a sealing skirt 46 for cooperating with the valve 100 to conform to the respective atrial floor to prevent paravalvular regurgitation of prosthesis. Applicants' application. Ser. No. 15/943,792 relates to an atrial sealing skirt and anchor which are tethered to one another and implanted integrally. According to the disclosure herein, the anchor is implanted independent of the tether and the atrial sealing skirt. It is to be appreciated, however, that components of this and Applicants' previously filed disclosure are interchangeable. For instance, the anchor of Applicants' prior disclosure may be implanted without having a tether coupled during delivery of the anchor. Rather, the tether systems described herein may also be used in connection with the anchors disclosed therein.

The Anchor Assembly

The components of anchor assembly 101 shown in FIGS. 3-6 include an anchor 75 having an anchor screw 17, an anchor cap 16 and a delivery cable 12 allowing delivery of a tether 18. The anchor cap 16 is coupled to the anchor screw 17. The delivery cable 12 is removably connected to the anchor cap 16. The anchor screw 17, as shown, is sized and configured as a helical screw to affix to an intracardiac wall. Optionally, however, the anchor screw 17 may be differentially sized (longer or shorter depending on the cardiac wall to which it attaches) and configured as an inclined plane, nail-like head, or as any other type of screw that would be known to those skilled in the art. In one aspect, the screw is composed of any known metal alloy, including, but not limited to, nitinol, titanium, or cobalt-chromium. In another aspect, the metal alloy of the screw 17 may be coated with biological tissue, such as bovine, ovine, porcine, or equine pericardium, or with any combination of anti-inflammatory drugs that might promote healing and limit inflammation. A tip 76 of the anchor screw 17 optionally is constructed of and/or coated with the same or different materials as the anchor screw 17, and may be fashioned as a blunt or sharp tip.

In use, the anchor 75 is secured to the cardiac wall by rotating the anchor screw 17 until the tip 76 is at a desired depth in the cardiac wall. The depth to which anchor screw 17 is screwed in is adjustable according to the location within the heart. For example, the anchor screw 17 may be implanted more deeply into the interventricular septum, for greater fixation, as opposed to the ventricular free wall, i.e. epicardial wall, where a shallower implantation is safer. By reversing the rotation of the anchor screw 17, the anchor 75 is removed safely from the cardiac wall, either to be repositioned, or to be removed entirely.

The anchor cap 16 comprises at least one locking arm 78 extending radially outwardly from the anchor cap 16. The locking arm 78 is sized and configured for releasably securing a portion of the tether 18 (described below) to the anchor cap 16. The at least one locking arm 78 moves between a first locked position, in which the locking member 78 extends a first distance away from the body of the anchor cap 16, and a second unlocked position in which the locking member 78 extends a second distance away from the anchor cap 16 that is less than the first distance. The anchor cap 16 comprises at least one biasing member (not shown), such as a spring, configured to urge each locking arm 78 to the first locked position. As shown, a plurality of locking arms 78 are provided and are spaced equally around the circumference of the anchor cap 16, though it is contemplated that the locking arms 78 need not be spaced equally.

Figure 3:
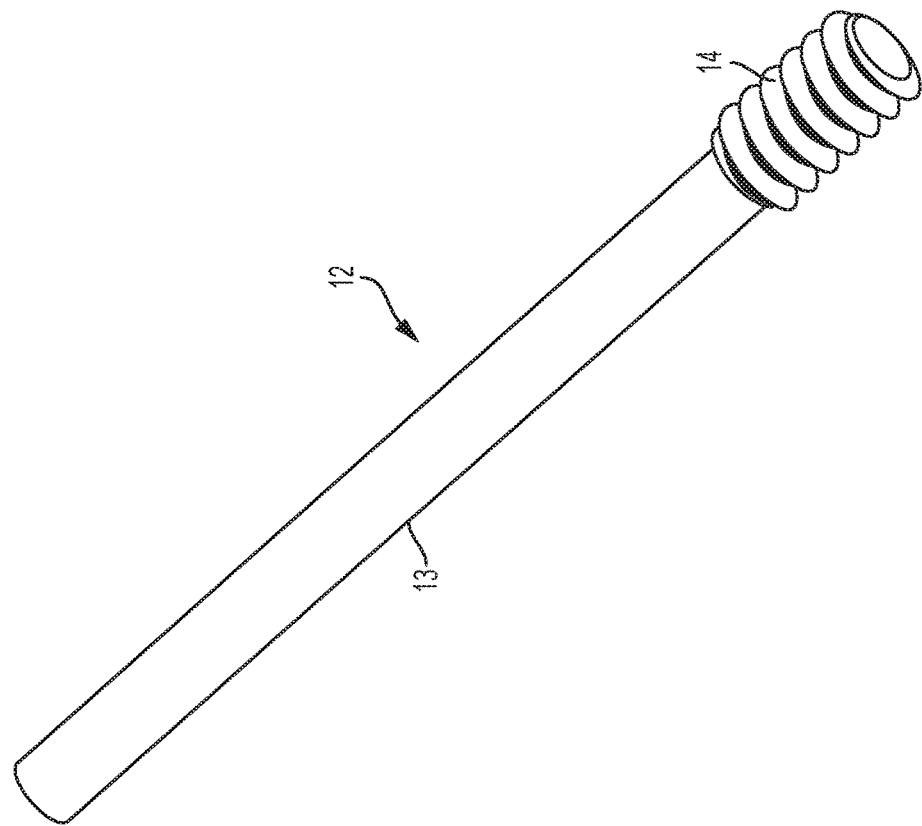
FIG. 3 is a perspective view of the delivery cable of an anchor delivery device for anchoring a tether to a cardiac wall.

Now referring to FIG. 3, the delivery cable 12 includes a flexible delivery wire 13 having a distal threaded end portion 14 positioned on or formed in the distal end of the delivery wire 13. The delivery wire is constructed of, but not limited to, stainless steel, nitinol or other metal alloys, with or without hydrophilic coatings, or with or without a polymer coating such as polytetrafluoroethylene (PTFE). The distal threaded end portion 14 is be sized and configured to selectively engage complementary threads formed in a cavity defined in a proximal end 77 of the anchor cap 16. See FIGS. 4 and 6. In use, the distal threaded end portion 14 advances, e.g., screws, into via the proximal end 77 of the anchor cap 16 to couple the anchor cap 16 to the distal end of the flexible wire 13. As described more fully below, the distal threaded end portion 14 is unscrewed from the proximal end of the anchor 75, detaching the flexible wire 13 from the anchor 75.

According to another aspect of the present invention, an expanding anchor assembly 102 is shown in FIGS. 7A-7C. As shown, the anchor assembly 102 is an interventricular anchor such as across the interventricular septum. The anchor assembly 102 includes an anchor cap 16 and locking arm 78 as described above for cooperating with the tether 18. The anchor assembly 102 also includes an anchor shaft 105 having a distal tip 107 configured for penetrating an intracardiac wall. The anchor shaft 105 and anchor screw 17 are comprised of at least two, and as shown three, shaft and anchor sectors 108. The sectors 108 are secured during implantation and intracardiac wall penetration by an internal tensioning means such as tensioning line 109 which splits into at least two, or shown three lines 109 terminating at the distal tip 107 of each section 108. Once the distal tip 107 of the anchor shaft 105 enters an intracardiac wall, such as the interventricular septum, the internal tensioning line 109 is released and relaxed, allowing the shaft sectors 108 to separate by the action of internal biasing members (not shown), such as, but not limited to, one or more springs located along one or more inner walls of the shaft sectors 108.

According to another aspect of the disclosure, as shown in FIGS. 25A-25F, an anchor assembly 103 is illustrated. The anchor 103 includes an anchor shaft 112 and an anchor screw 114. As shown, the anchor screw 114 has a helical configuration and extends distally from an anchor screw base 115. The anchor screw base 115 defines at least one, or a plurality as shown, of anchor flanges 116 and recessed areas 117 therebetween. The anchor shaft 112 includes at least one or, as shown, a plurality of locking members 118 shown in FIG. 25B. Locking members 118 are biased, such as by a spring (not shown), radially outwardly from the anchor shaft 112. An anchor connector 120 and connector rod 121 cooperate with the anchor shaft 112 to rotate the anchor screw 114. The anchor connector 120 defines at least one or, as shown, a plurality of apertures 122 configured for receipt of the anchor flanges 116. Accordingly, the anchor connector 120 and connector rod 121 are matingly connected to the anchor shaft 112, thereby urging the locking members 118 inward. The cooperating of the apertures 122 and the flanges 116 integrate the anchor connector 112 and the anchor screw base 115. Rotation of the connector rod 121 thereby rotates the anchor screw 114 for interventricular or epicardial implantation into an intracardial wall.

Figure 25A:
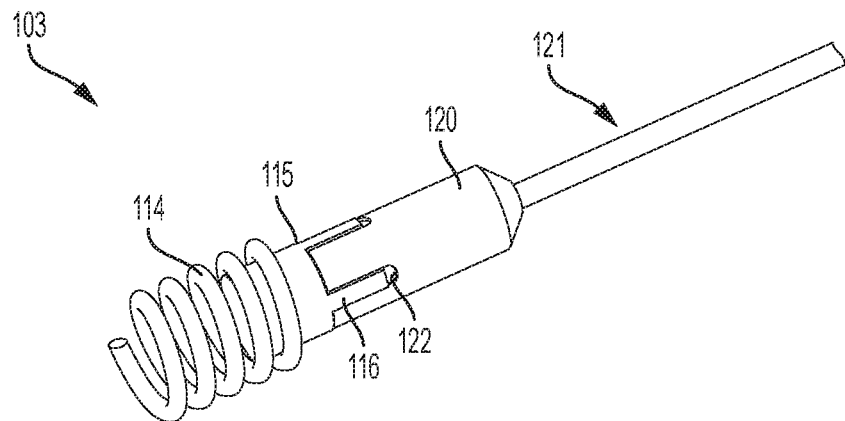
FIGS. 25A-25F are perspective views of an anchor having an anchor screw and anchor cap configured for receipt of connecting ring and a tethering system illustrated in sequential steps.
Figure 25B:
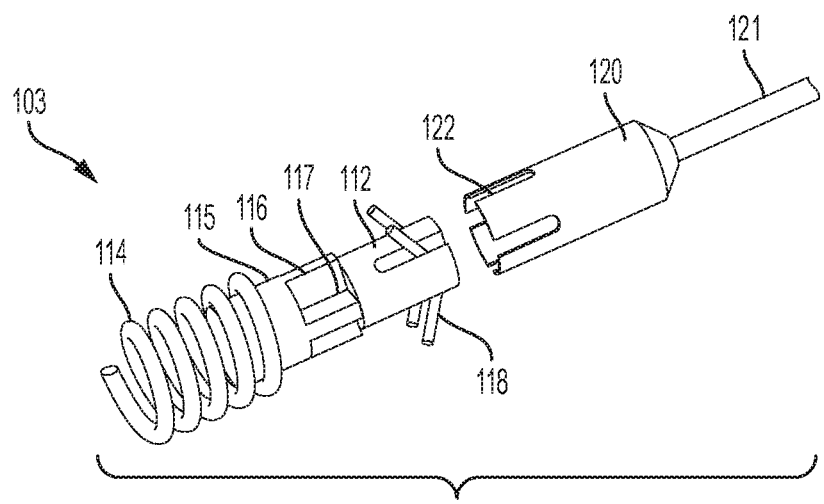
Figure 25C:
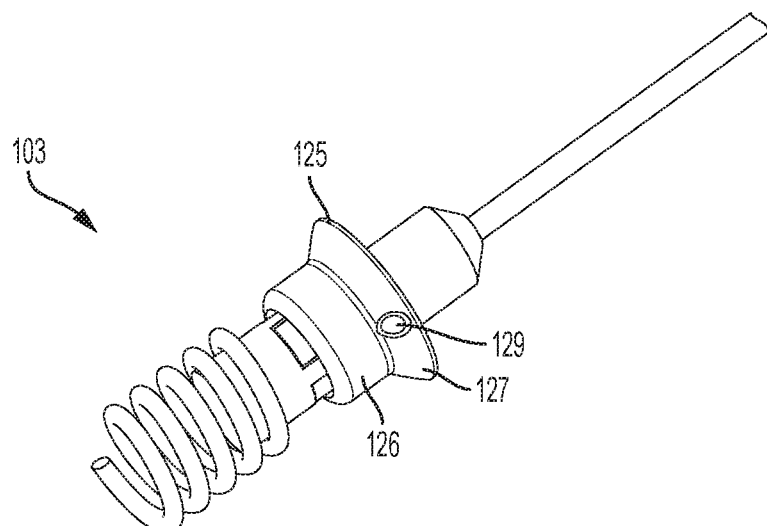
Figure 25D:
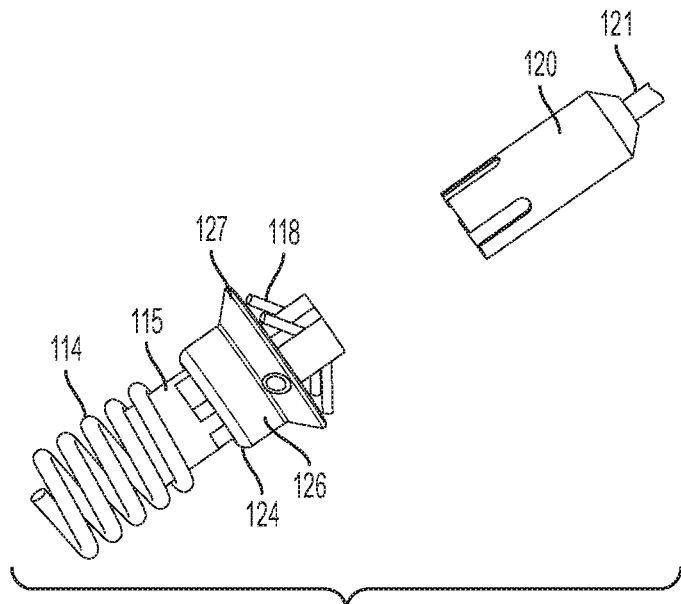
Figure 25E:
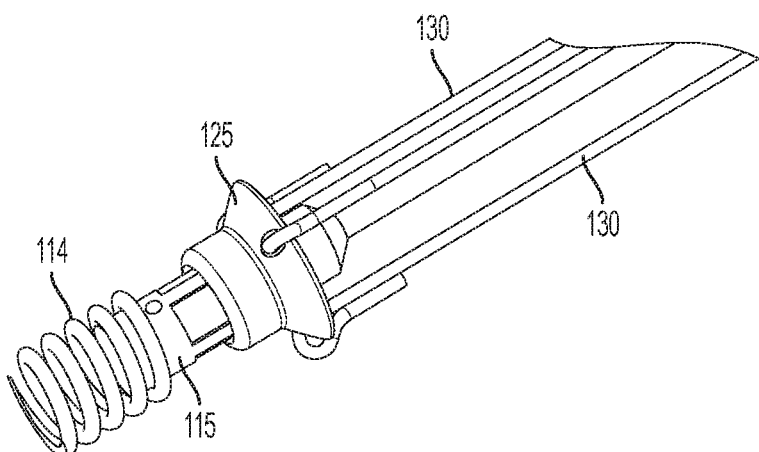
Figure 25F:
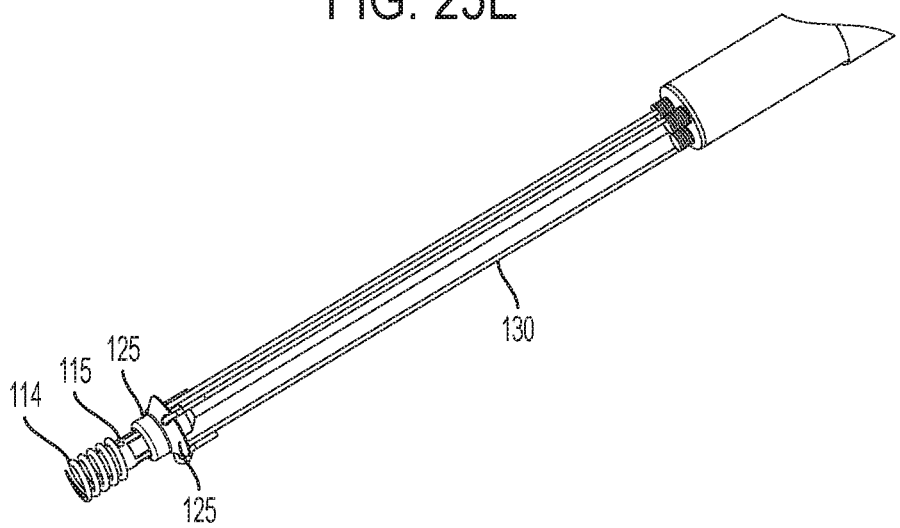

After the anchor screw 114 has been implanted, a tether ring 125 is applied over the connector rod 121 and anchor connecter 120 and abuts the proximal end of the anchor screw 114. The tether ring 125 includes a generally cylindrical first distal portion 126 and a second proximal portion 127 having a diameter greater than the first portion 126. The second portion 127 defines at least one or, as shown, a plurality of apertures 129 configured for receipt of tether rods 130 as shown in FIGS. 25E and 25F. As shown in FIG. 25D, the anchor connector 120 and connector rod 121 are removed. The locking members 18 are urged radially outward so as to engage the second portion 127 of the tether ring 125 to lock the tether ring 125 on the anchor screw base 115. Tether rods 130 are operative as described above for cooperating with an atrial sealing skirt 46.

The Tether Assembly

Figure 5:
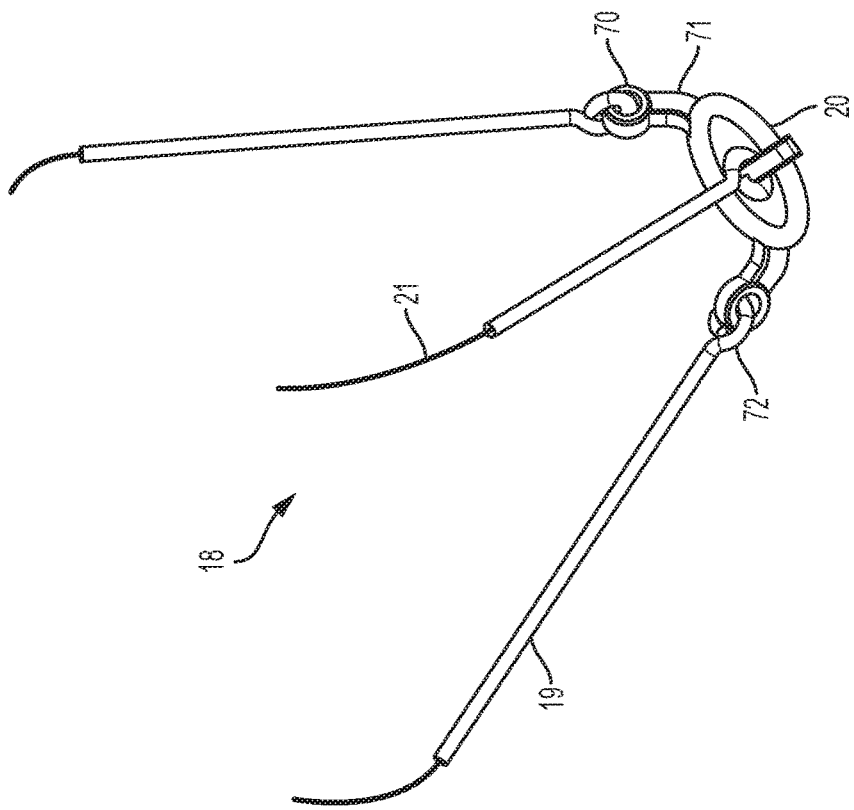
FIG. 5 is a perspective view of a tether for anchoring the atrial sealing skirt to the anchor.

When the flexible wire 13 is coupled to the anchor 75, the flexible wire serves as a guide rail for the advancement of the tether 18 to the anchor 75. The tether 18 includes one or more tether rods 19 rotatably connected to a docking ring 20. The tether rods 19 are connected to an eyelet 70 defined by docking ring arms 71 as shown in FIG. 5. The tether 18 is advanced over the flexible wire 13 of the delivery cable 12, and the docking ring 20 of the tether 18 depresses the at least one locking arm 78 of the anchor cap 16 to the second unlocked position. With the locking arm 78 in the second position, the tether 18 advances over the locking arm 78 on the anchor cap 16 until the docking ring 20 abuts and/or is adjacent to a distal end 79 of the anchor cap 16. At this point, the biasing member of the anchor cap 16 urges the at least one locking arm 78 to the first locked position, thereby releasably coupling the docking ring 20, and thus the rest of the tether 18, to the anchor 75.

In one aspect, when coupled to the anchor 75, the tether 18 rotates about a longitudinal axis of the anchor a full 360 degrees. Optionally, in another aspect, the tether 18 may be constrained to lesser degrees of rotation by interaction of a portion of the tether 18 with the at least one locking arm 78.

Figure 6:
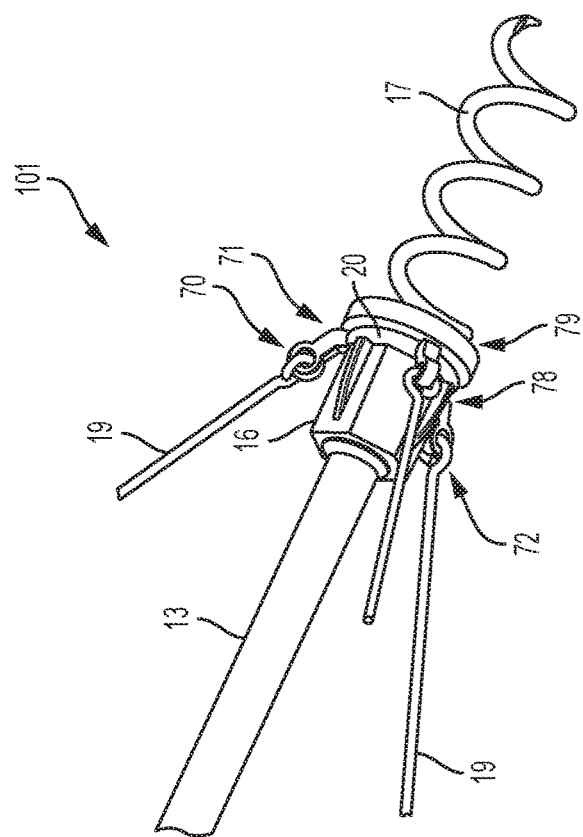
FIG. 6 is a perspective view of the anchor assembly, comprised of the tether, for connecting the atrial sealing skirt to the anchor, coupled to the anchor, for anchoring the tether to a cardiac wall.

As shown in FIG. 6, in one aspect, the tether 18 comprises at least one docking ring arm 71 coupled to the docking ring 20, and at least one tether rod 19 coupled a docking ring arm 71. As shown, a distal end of the docking ring arm 71 is securely coupled to or formed monolithically with the docking ring 20. As shown, the at least one docking ring arm comprises a plurality of docking ring arms 71. As shown, the plurality of docking ring arms 78 are spaced equally around the circumference of the docking ring, though it is contemplated that the docking ring arms 71 need not need spaced equally. An eyelet 70 is defined by the docking ring arm 71. The tether rod 19 includes a tether rod hook 72 configured for cooperating with the eyelet 70.

A proximal end of each docking ring arm 71 is rotatably coupled to a distal end of a respective tether rod 19. A tether rod hook 72 is defined by the tether rod 19 as shown and is either coupled to or formed monolithically with the distal end of each tether rod 19. In another aspect, the eyelet 70 and the tether rod hook 72 are sized and configured so that the tether rod hook 72 is inserted into the eyelet 70 to securely, rotatably couple the tether rod 19 to the docking ring 20. In use, each tether rod hook 72 rotates about the circumference of the eyelet 70. As shown in FIG. 5, the proximal end of each tether rod is coupled to a cord 21. The tether rod 19 and the tether rod hook 72 may be composed of any metal alloy.

The tether 18 is configured to cooperate with any intracardiac anchor including, but not limited to, the interventricular and epicardial anchors disclosed herein and the interventricular and epicardial anchors of Applicants' prior disclosure incorporated herein by reference.

The Anchor Delivery Device

Figure 8A:
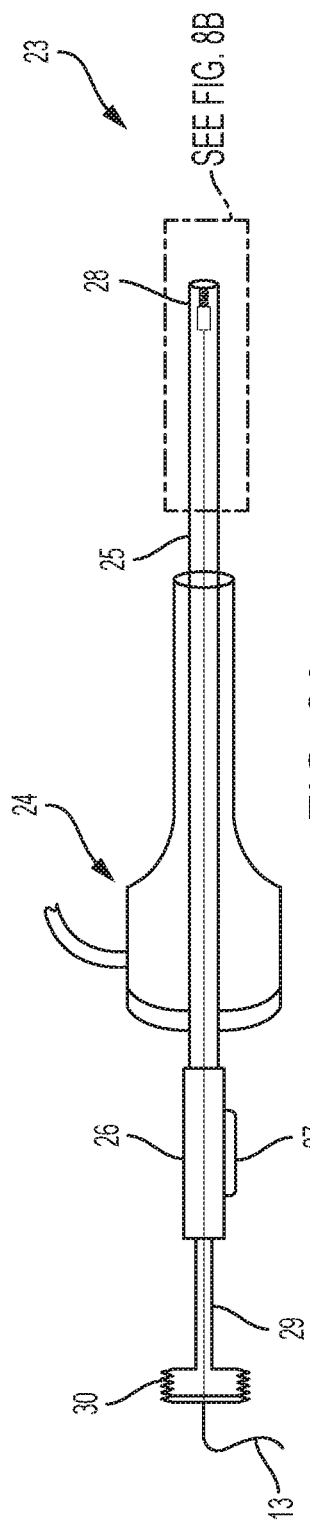
FIG. 8A is a side elevational view of the anchor delivery device.
Figure 8B:
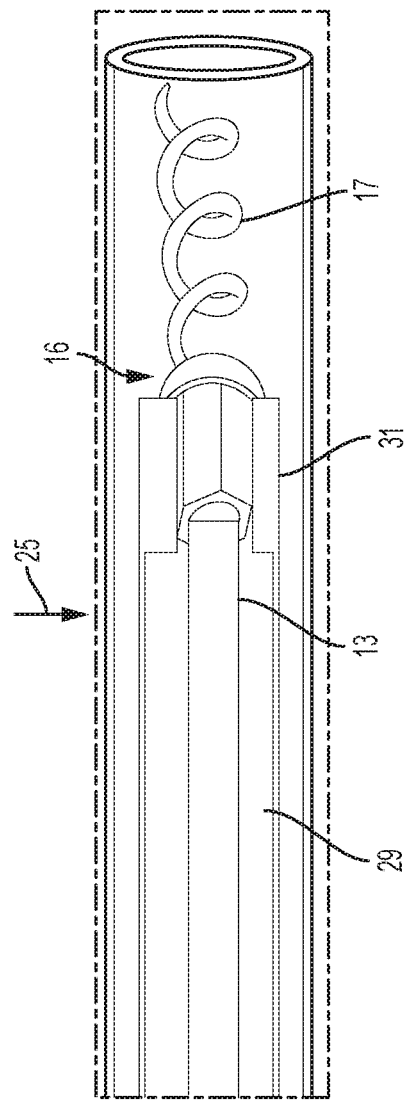
FIG. 8B is a side view of the anchor delivery device shown within the delivery sheath.
Figure 8C:
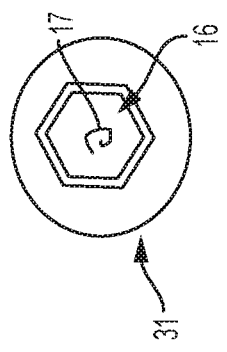
FIG. 8C is an end view of the anchor delivery device.

Referring now to FIGS. 8A-8 C and 9A-9B, the anchor delivery device 23 for positioning and deploying the anchor cap 16 at the desired position is illustrated and pertains to the components of anchor assembly 101 shown in FIGS. 3-6 and the anchor assembly 102 shown in FIGS. 7A-7C. The delivery device 23 comprises an anchor delivery guide 25 and an anchor delivery rod 29. The anchor delivery guide has a distal end 28 and an inner guide lumen sized and configured so that at least one portion of the anchor delivery rod 29 extends there through. At least a portion of anchor delivery guide 25 is flexible so that the distal end 28 of the anchor delivery guide 25 is positioned at or adjacent to an intracardiac wall 7.

The anchor delivery rod 29 is configured to securely attach the anchor screw 17 to the intracardiac wall 7. The anchor delivery rod 29 has a distal end 31, an opposed proximal rotating handle 30, and an inner rod lumen extending there between. The inner rod lumen is sized and configured so that at least a portion of the delivery cable 12 extends there through. At least a portion of the anchor delivery rod 29 is flexible so that a rod tip 31 at the distal end of the anchor delivery rod 29 may be positioned at or adjacent the intracardiac wall 7.

A portion of the anchor cap 16 (as shown, the portion proximal to the anchor cap distal end 79) is received by and extends within the anchor rod tip 31. The outer configuration of the anchor cap 16 proximal portion includes a first surface configuration and the inner wall configuration of said anchor rod 29 distal portion has a second configuration wherein the first and second configuration mate. Thus, when the anchor cap 16 is positioned in and engaged with the anchor rod tip 31, rotation of the anchor delivery rod 29 rotates the anchor cap 16. In this position, the anchor screw 17 extends distally from the anchor delivery rod 29 as illustrated in FIG. 8B and the delivery cable 12 extends through the inner rod lumen of the anchor delivery rod 29.

The anchor delivery device 23 also includes a guide handle 26 having a deflection knob 27 coupled to the anchor delivery guide 25. The guide handle 26 and the deflection knob 27 are configured and used to help guide the distal end 28 of the anchor delivery guide 25 to the intracardiac wall 7. A rod handle 30 is coupled to the anchor delivery rod 29 wherein rotation of the rod handle rotates the rod tip 31 and the anchor cap 16 when the anchor cap is positioned in the anchor rod tip 31.

As shown, in FIG. 8A a sheath 24 is configured to receive the anchor delivery guide 25. The sheath 24 is in fluid communication with the anchor delivery guide so that fluids, such as heparinized saline and the like surrounds the anchor delivery guide through the sheath 24. A central sheath channel 33 (FIG. 9B) is defined in the sheath 24 to provide communication with the inner guide lumen of the anchor delivery guide 25 for the anchor delivery rod 29 and other system components to extend through the central sheath channel 33.

The Method of Implanting the Anchor

Figure 9B:
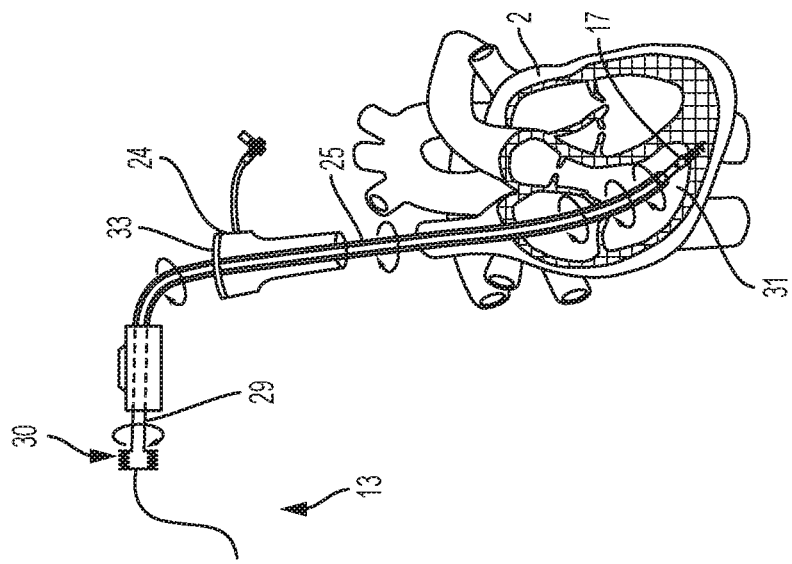
FIG. 9B is a perspective view of the anchor being implanted into the intracardiac wall.
Figure 9A:
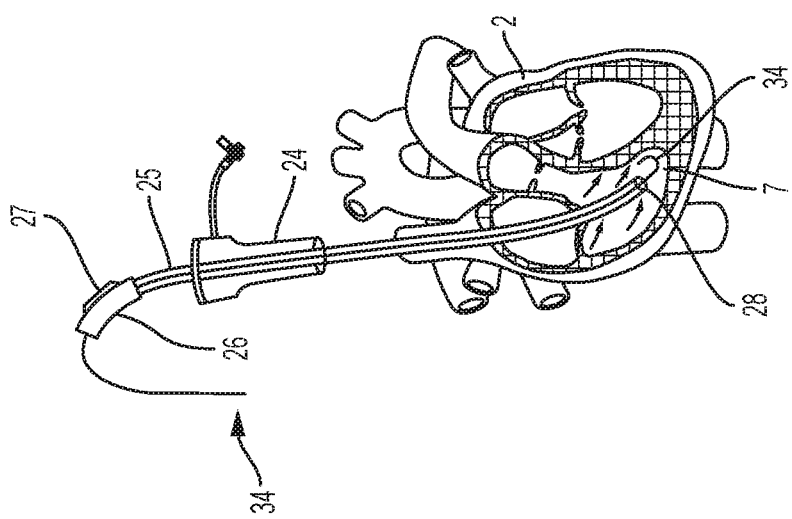
FIG. 9A is a perspective view of the anchor delivery device being positioned in the right ventricle.

As shown in FIG. 9A, in the tricuspid annulus, for example, a J-wire 34 is endovascularly guided by the user to the intracardiac wall 7. The anchor delivery device 23 is then guided over the J-wire until the distal end 28 of the anchor delivery guide 25 is positioned at or adjacent the intracardiac wall 7. FIGS. 9-11 illustrate the anchor assembly 101 of FIGS. 3-6 implanted into an intracardiac wall that is an epicardial wall. Anchor assembly 101 may also be implanted into an interventricular wall. The J-wire is, for example and without limitation, a 0.025" or 0.035" J-wire. Of course, J-wires having other diameters are contemplated. The anchor cap 16 is coupled to the distal end 31 of the anchor delivery rod 29. The anchor delivery rod 29 is then be inserted through the inner guide lumen of the anchor delivery guide 25 until the anchor cap 16 and the distally extending anchor screw 17 are positioned at or adjacent the intracardiac wall 7.

The anchor assembly 102 of FIGS. 7A-7C may also be implanted and guided by the J-wire 34 such as into the interventricular wall as the intracardiac wall 7 shown. The anchor assembly 103 of FIGS. 25A-25F may also be implanted and guided by the J-wire 34 into an intracardiac wall 7, such as an interventricular wall or an epicardial wall.

Figure 10B:
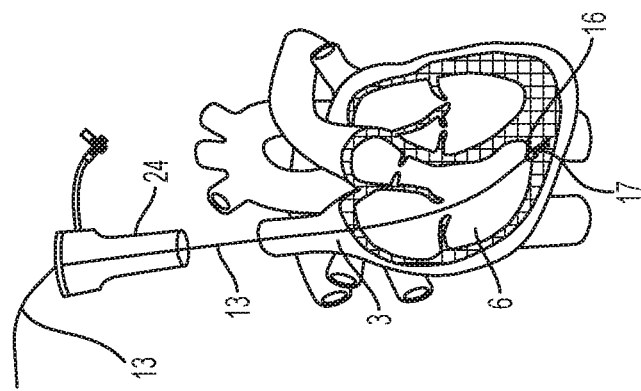
FIGS. 10A and 10B illustrate the anchor delivery being removed.
Figure 10A:
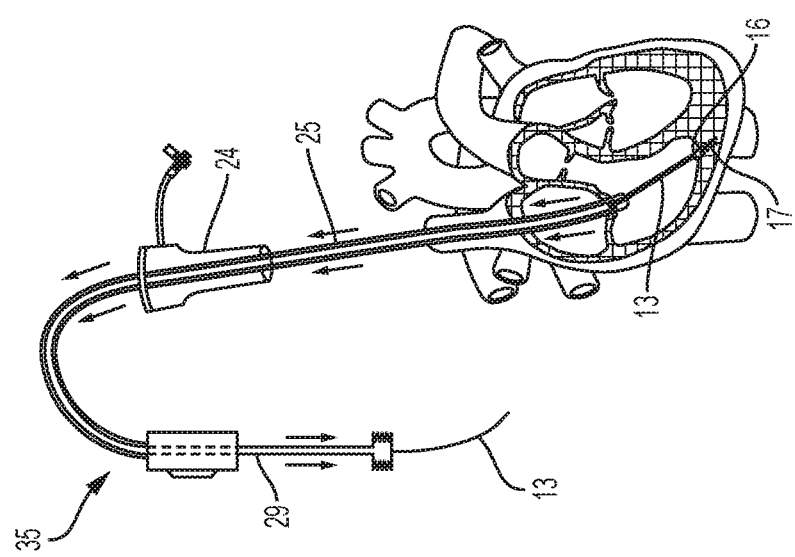

With the anchor screw 17 of anchors systems 101, 102 or 103 positioned adjacent to the intracardiac wall 7, the rotating handle 30 of the anchor delivery rod 29 or 121 is rotated to cause corresponding rotation of the anchor cap 16 as illustrated in FIG. 9B. For example, the rotating handle 30 is rotated in a first direction to cause corresponding rotation of the anchor cap 16. The anchor screw 17 coupled to the anchor cap 16 also rotates and screws into a portion of the intracardiac wall until the anchor cap 16 is adjacent to the apex wall. Note that in this position, the anchor screw 17 may or may not extend completely through any intracardiac wall, but trans-apical access is not necessary. Upon placement of the anchor cap 16 in the desired position, the anchor delivery rod 29 and the anchor delivery guide 25 are retracted from the heart 2 as illustrated in FIG. 10A. As shown in FIG. 10B, after placement of the anchor cap 16, the flexible wire 13 of the delivery cable 12 extends from the anchor cap 16, through the tricuspid annulus, and through the right atrium 3.

The Atrial Sealing Skirt

As shown in FIGS. 14A, 14B, 23A, 23B, 24A and 24B the system 1 comprises a heart valve 100 having an atrial sealing skirt 46 with a skirt top brim 47 extending circumferentially along the upper end of the valve 100. The atrial sealing skirt 46 includes an atrial skirt body 48, shown substantially cylindrical, and the atrial skirt top brim 47 which is configured to conform to an atrial floor 4, such as the right atrial floor as shown. The atrial sealing skirt 46 is coupled to the anchor 75 by the tether 18 as described herein. The cord 21, fused or otherwise coupled to the tether rod 19 of tether 18, connects the valve 100 to the anchor 75 when the anchor 75 is fixated to an intracardiac wall 7.

Figure 2:
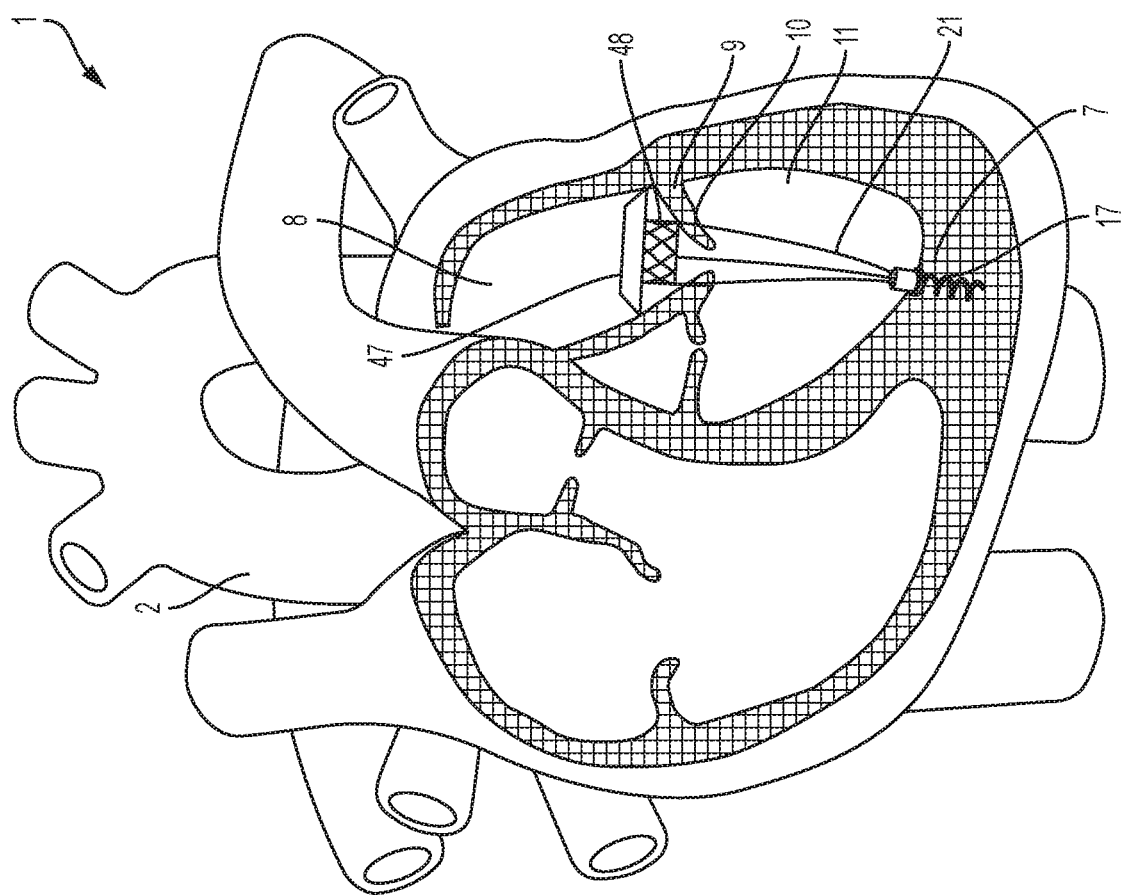
FIG. 2 is a cut-away perspective view of a heart showing the transcatheter atrial sealing skirt system positioned across the mitral valve in the heart.
Figure 4:
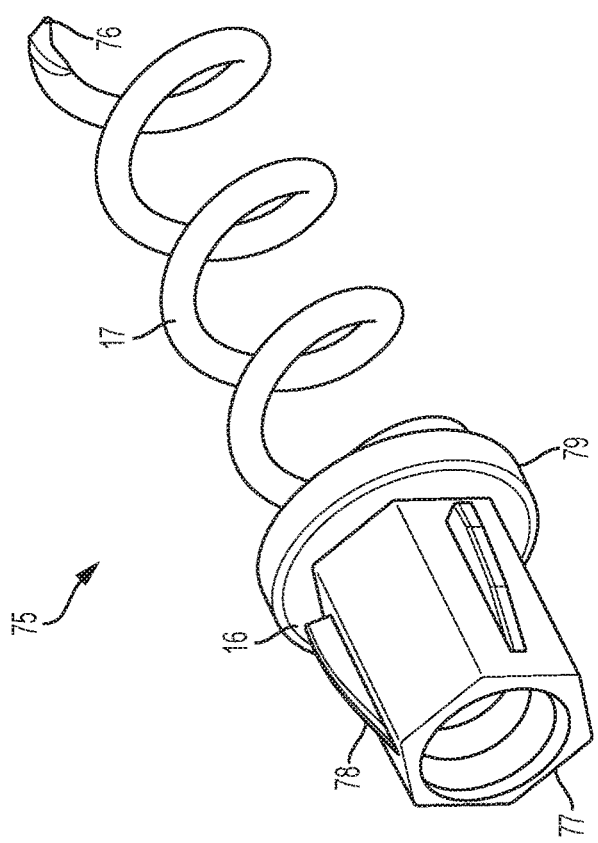
FIG. 4 is a perspective view of an anchor for anchoring a tether to a cardiac wall.

The transcatheter atrial sealing skirt 46 is sized and configured to sit in the tricuspid valve (in the example shown) between the right atrium 3 and the right ventricle 6 as illustrated in FIG. 1. The sealing skirt 46 may be pre-assembled with valve leaflets 110 as an integrated valve 100 (FIG. 23A, 23B) or the sealing skirt 46 may be constructed without valve leaflets and serve as a docking system for a separate transcatheter valve (FIG. 24A, 24B). This is by way of example. Optionally, however, with slight variations, the valve is sized and configured to be positioned in the mitral annulus between the left atrium 8 and the left ventricle 11 as illustrated in FIG. 2. Accordingly, then, with slight variations, these devices, systems, and methods are used for either the tricuspid or mitral valves and may be endovascularly placed by a venous structure including, but not limited to, either internal jugular vein, either subclavian vein, either subclavian vein or either femoral vein.

The atrial sealing skirt 46 is self-expanding (i.e. the skirt is compressible so that it fits through a catheter of system 1) and composed of nitinol, but may also contain elements made of, but not limited to, stainless steel, nitinol or other metal alloys. In another aspect, the atrial sealing skirt has a lower diameter that is smaller than or approximately equal to the annulus at the site deployment 5 (tricuspid annulus) or site deployment 10 (mitral annulus), thereby preventing or reducing apposition to the fragile tricuspid annulus, and preventing or reducing constraint of the mitral annulus.

At least one conduit 53 is defined in the outer wall of the atrial sealing skirt 46 as illustrated in FIGS. 12C, 14A and 14B, 23A and 23B and 24A and 24B. Each conduit is sized and shaped so that a portion of the cord 21 (attached at the proximal end to suture 45, as illustrated by FIGS. 12A and 12B) extends through the conduit 53, thereby connecting the tether 18 to the atrial sealing skirt 46, allowing free movement until the skirt 46 is locked in place. In a further aspect, the atrial sealing skirt 46 has anchoring elements (not shown) positioned along its outer diameter. These anchoring elements allow fixation to the tricuspid or mitral annulus and/or leaflets, but are not necessarily used a primary fixation mechanism.

The at least one cord 21 is coupled to the tether rod 19 of the tether 18, and the proximal portion of cord 21 is coupled to suture 45. In one aspect, the cord may be a strong yet flexible cord such as, for example and without limitation, an expanded polytetrafluoroethylene (ePTFE) or ultra-high-molecular-weight polyethylene (UHMWPE, UHMW) cord. In use, described more fully below, a central portion of the cord 21 (between the distal end and the proximal end) extends through and/or be coupled to the atrial sealing skirt 46 to hold the skirt in the desired position relative to the tricuspid annulus or the mitral annulus.

Figure 23A:
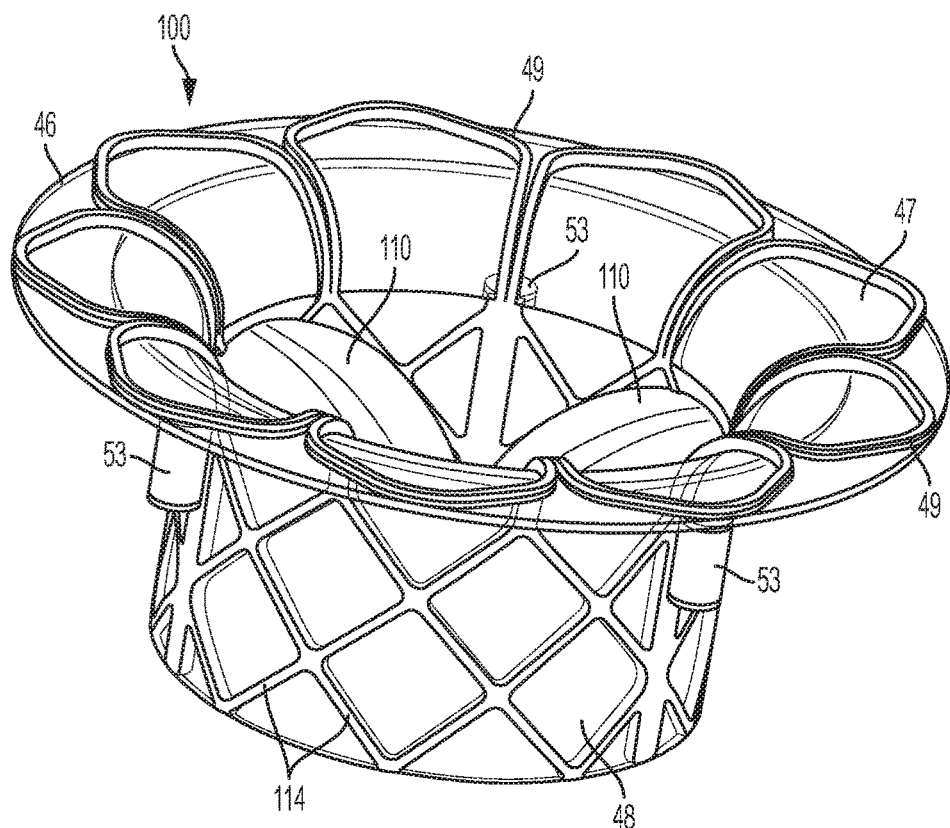
FIGS. 23A and 23B are perspective and top plan views of the atrial sealing skirt with a valve, composed of valve leaflets, integrated into the skirt.
Figure 23B:
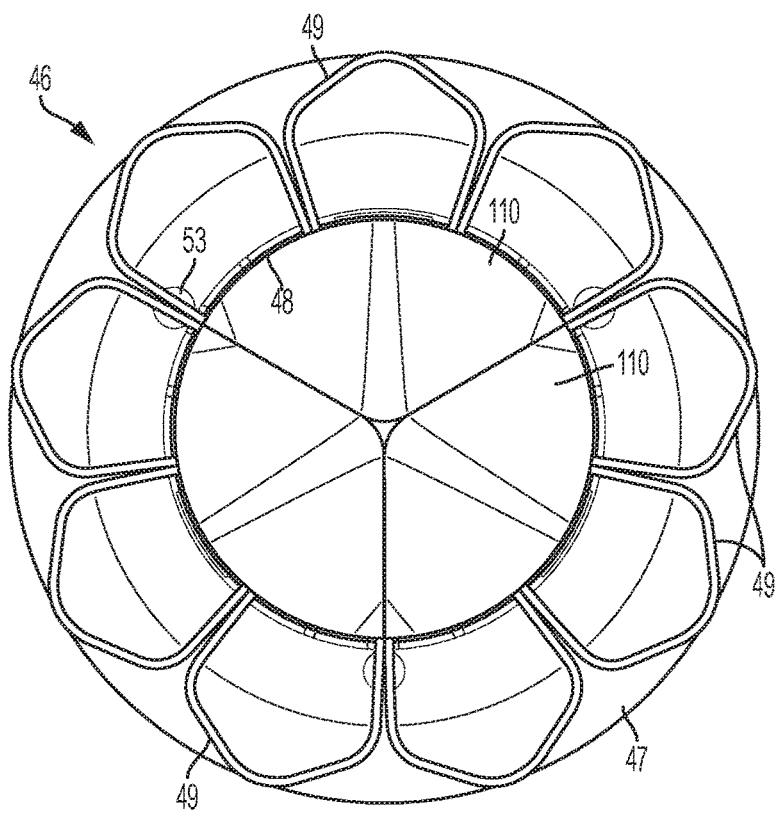
Figure 24A:
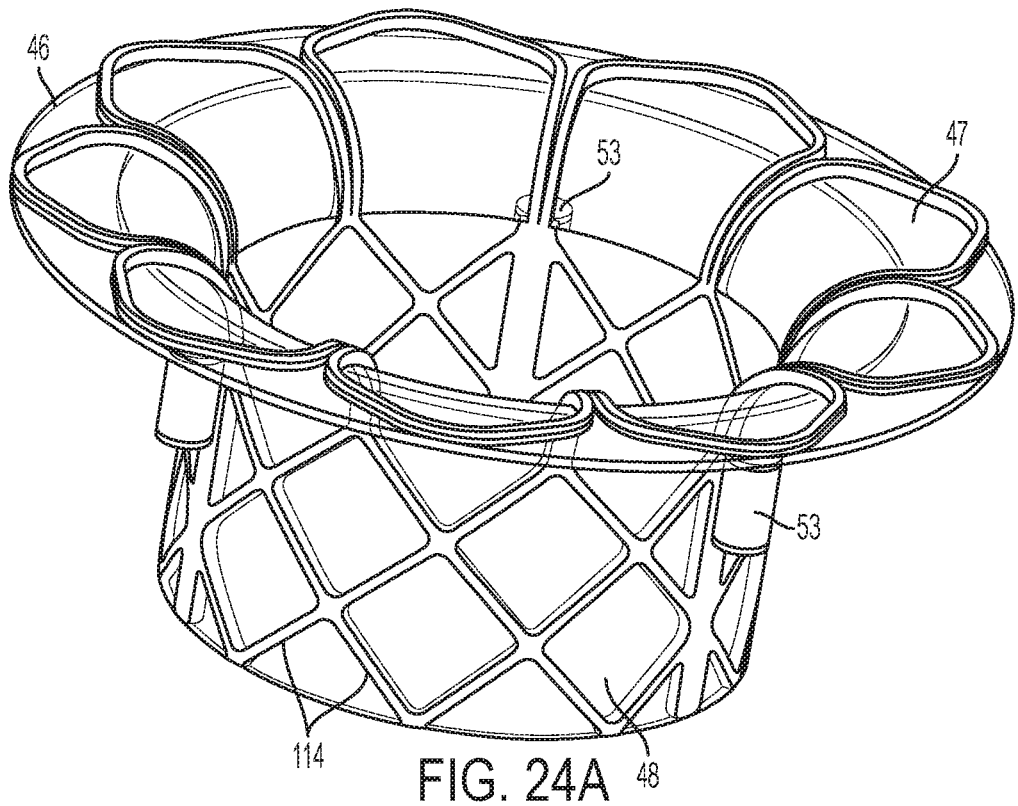
FIGS. 24A and 24B are perspective and top plan views of the atrial sealing skirt for receipt of a valve.
Figure 24B:
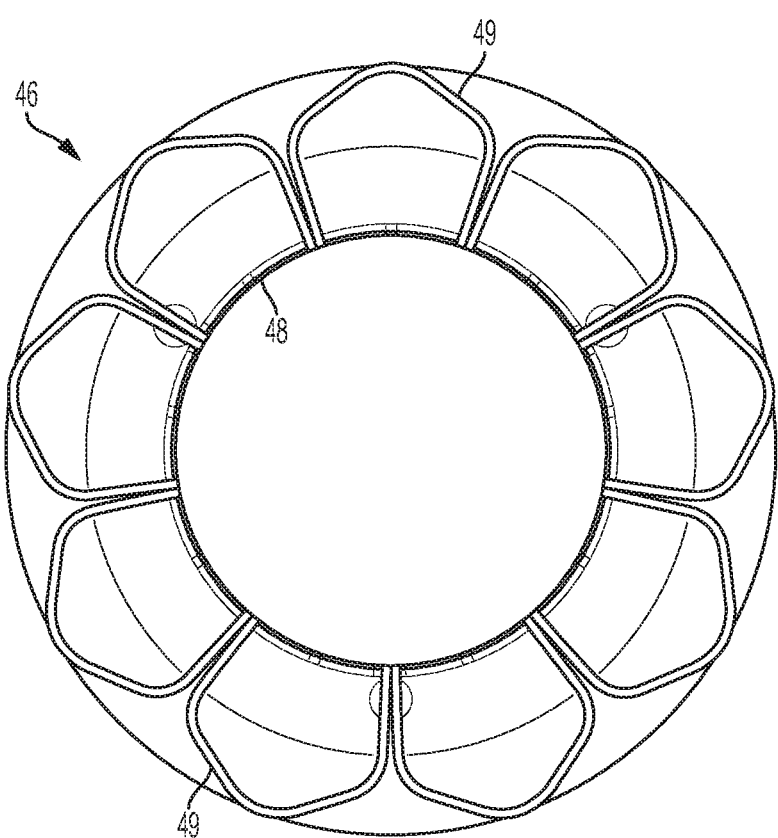

FIGS. 23A and 23B also illustrate the atrial sealing skirt 46. The sealing skirt 46 is an integrated valve 100, composed of leaflets 110 extending radially inwardly from the sealing skirt body 48. The leaflets 110 are composed of bovine, equine, or porcine pericardial leaflets. The atrial sealing skirt 46 may be used as a docking system for any conventional valve, or may be pre-assembled to include valve 100 composed of leaflets 110. If the atrial sealing skirt 46 contains valve 100 composed of leaflets 110 sewn to the interior of the sealing skirt body 48, this configuration will function as any conventional valve does, with the leaflets 110 opening during diastole (relaxation of the heart) allowing blood to enter from the right atrium 3 into the right ventricle 6, or from the left atrium 8 into the left ventricle 11, and closing during systole (contraction of the heart), preventing blood from regurgitating from either the right or left ventricle back into the right or left atrium, respectively.

As shown in FIGS. 14A and 14B, 23A and 23B, and 24A and 24B, the atrial sealing skirt 46, defined by atrial skirt body 48 and atrial skirt top brim 47, includes a membrane-like material and the sealing skirt 46 has a diameter greater than the annulus at the site of deployment. For example, the atrial sealing skirt 46 may have a skirt diameter greater than the diameter of either the tricuspid or mitral annulus. In another aspect, the atrial skirt is formed by, but not limited to, synthetic materials from the classes consisting of polycarbonate, polyurethane, polyester, expanded polytetrafluoroethylene (ePTFE), polyethylene terephthalate (PET), silicone, natural or synthetic rubbers, or a combination thereof. The atrial skirt 46 may also be covered with adult or juvenile bovine, ovine, equine, or porcine pericardium. Optionally, at least a portion of the atrial sealing skirt 46 may be formed from alternative materials, such as, for example and without limitation, polyurethane foam or other polymers.

In another aspect, at least a portion of the atrial sealing skirt 46 has one or more fixation members (not shown) along its length, allowing further anchoring to the right atrial floor and/or other portions on the atrial side of the tricuspid annulus, preventing migration of the atrial sealing skirt 46 into the proximal right atrium 3, thereby preventing instability (e.g. rocking) and paravalvular regurgitation of prosthesis. Optionally, with slight modifications, these fixation members permit further anchoring of the atrial sealing skirt 46 to the left atrial floor and/or portions on the atrial side of the mitral annulus, preventing migration of the atrial sealing skirt 46 into the proximal left atrium 8, also preventing instability (e.g. rocking) and paravalvular regurgitation of prosthesis.

The atrial sealing skirt 46 comprises at least an atrial skirt body 48 and an atrial skirt top brim 47. As shown, the atrial skirt body 48 is a cylinder and has a variable length and diameter. It is selectively composed of either laser-cut or molded nitinol, but also may contain elements of any other metallic alloy, and may be covered along any portion of its circumference or length with either biological membranes or synthetic materials mentioned above. As shown, the top brim 47 extends radially outwardly from the skirt body 48 and downwardly, forming a substantially concave top brim with the concavity facing the right atrial floor 4 or left atrial floor 10. The brim 47 extends circumferentially around the upper end of the skirt body 48.

At least one, or shown a plurality of, flexible extension members 49 are provided and which may, for example, be composed of, but not limited to, laser-cut or molded nitinol attached to the top of the skirt body by the extension member base 50 and terminating in the extension member tip 51. Between one or more extension members 49 is an elastic sealing membrane 52 extending perpendicular to adjacent extension members 49. As shown in FIGS. 14A and 14B, the extension member 49 may extend radially outwardly and substantially linearly, but this is exemplary. As shown in FIGS. 23A, 23B, 24A and 24B, the extension members may be nonlinear and generally U-shaped. As shown, the sealing membrane 52 extends circumferentially around the skirt brim 47. It may extend only a portion of the circumference as well. The sealing skirt body 48 includes a plurality of supports 114 which, like the extensions members 49 of the top brim 47, may, for example, be composed of, but not limited to, laser-cut or molded nitinol. As shown, the supports 114 form a lattice-like configuration, but other configurations are contemplated including, but not limited to, vertically extending supports.

Figure 17B:
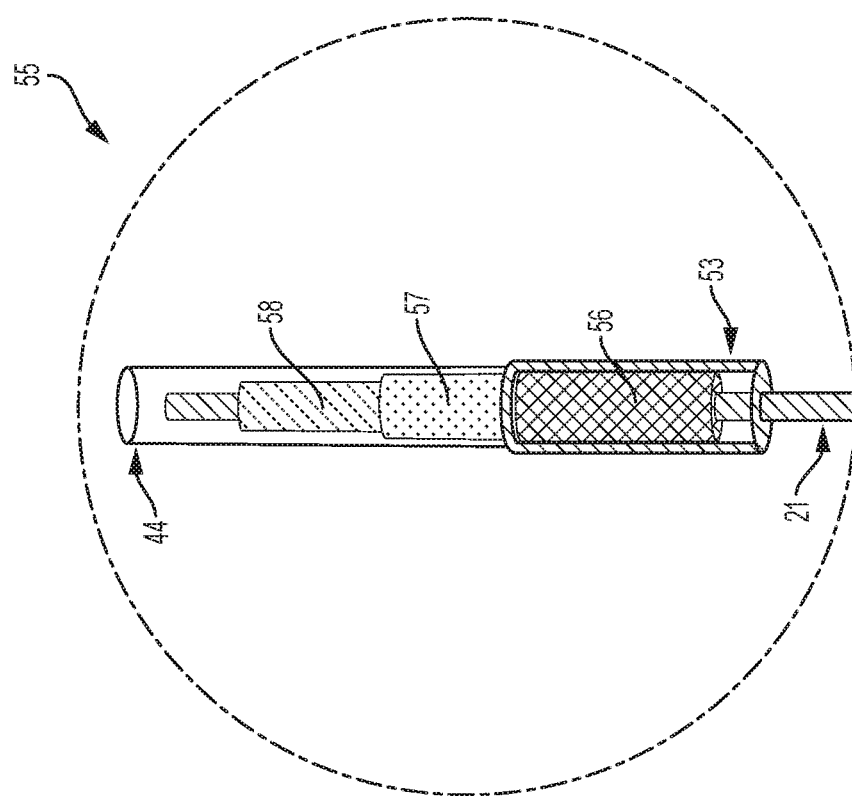
FIG. 17B is an enlarged side elevational view of the locking system.

The sealing member 52 is composed of either biological tissues or synthetic fabrics as mentioned above. In one aspect, the synthetic fabric is either braided or knit, allowing the "stretchability" required to conform to atrial floor topography, including the ability to cover and seal intracardiac leads, such as permanent pacemaker leads 66 as shown in FIGS. 16A and 16B. As shown in FIG. 16A, the atrial skirt top brim 47 conforming to the right atrial floor 4 and sealing around intracardiac lead 66, according to one aspect. In FIG. 16B, the extension member 49 is attached to the atrial skirt body 48 via the extension member base 50, and the extension member tip 51 is bending downwards, allowing the elastic sealing membrane 52 to wrap around the top of intracardiac lead 66, and thereby preventing regurgitation around the lead. This conformation requires downward force applied via one or more atrial positioning rods 44, attached to one or more conduits 53, and locked into place via one or more detachable locks 56 (FIG. 17B) integrated inside the atrial end of the conduits 53 as described herein.

The Tether and Atrial Sealing Skirt Delivery Assemblies

According to the method described above, the anchor 75 is introduced by the anchor delivery device 23 and secured to an intracardiac wall and the anchor 75 comprising the anchor screw 17 has been implanted into an intracardiac wall. Anchor cap 16 and delivery cable 13 remain within the heart and are ready to receive the tether 18 described above.

Referring now to FIGS. 11A, 11B, 11C and 11D and as described above, the tether 18 is advanced over the flexible wire 13 of the delivery cable 12 through the atrial skirt delivery system shown in the form of delivery sheath 137. The tether 18 locks onto anchor cap 16 by coupling the docking ring 20 to the anchor cap 16. Coupled to at least one tether rod 19 is at least one cord 21 that extends from the tether rod 19. The at least one cord 21 is connected proximally to at least one suture 45, which extends outside the body via the central lumen 33 of the delivery sheath 137. Once the tether is locked to the anchor cap 16, the sheath 137 is retracted as shown in FIG. 11C, leaving the implanted anchor 16, tether 18, cords 21 and suture extending from the implantation site. In the aspect shown in FIG. 11C, a tether delivery sheath 137 is provided as a second delivery guide and is a different sheath than the atrial sealing skirt delivery guide sheath 38, which is the third delivery guide, described below. Therefore, the tether sheath 137 is removed and the atrial sealing skirt delivery guide sheath 38 is applied. This may be achieved in a single step, however, as shown in FIGS. 12A-12B wherein the same sheath 38 delivers both the tether 18 and atrial sealing skirt 46 with the same sheath and constitutes the second delivery step.

Referring now to FIGS. 12A and 12B, the atrial sealing skirt delivery system 37 for positioning and deploying the atrial sealing skirt 46 at the desired deployment sites 5 or 10 is illustrated. The atrial sealing skirt delivery system 37 comprises an atrial sealing skirt delivery guide 38, a nosecone 43, an atrial sealing skirt deployment knob 39 and at least one atrial positioning rod 44. The atrial sealing skirt delivery guide 38 has a distal end 41, an opposed proximal atrial sealing skirt deployment knob 39 and an inner guide lumen 40 extending therebetween. The inner guide lumen 40 is sized and configured so that the atrial sealing skirt 46 and other system components are selectively and removably inserted therethrough. At least a portion of the atrial sealing skirt delivery guide 38 is flexible so that a tip 41 at the distal end of the anchor delivery guide 25 are positioned past the deployment site 5 and into the right ventricle 6. Alternatively, the distal tip 41 is positioned past deployment site 10 and into the left ventricle 11.

The atrial sealing skirt deployment knob 39 is coupled to the proximal end of the atrial sealing skirt delivery guide 38. The atrial sealing skirt deployment knob defines a central channel 60 which is in fluid communication with the inner guide lumen 40. Accordingly, the atrial positioning rod 44, the guide wire 13 and/or the at least one suture 45 may extend through the central channel 60 and into the inner guide lumen 40. As shown, the atrial sealing skirt deployment knob 39 is rotatable and configured such that rotation of the knob 39 in a first direction causes distal tip 41 of the atrial sealing skirt delivery guide 38 around the atrial sealing skirt 46 to be retracted, allowing atrial sealing skirt 46 to expand. The nosecone 43 may be any conventional nosecone coupled to the atrial sealing skirt delivery guide 38 and configured to guide the atrial sealing skirt 46 to the deployment site 5.

The Locking System

Figure 13B:
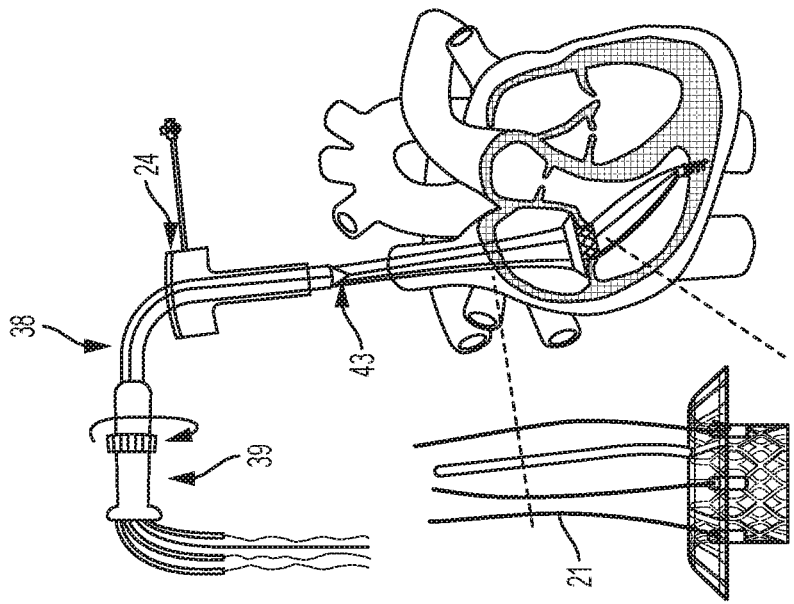
FIG. 13B is a perspective view of the atrial sealing skirt locked into position in the tricuspid annulus by atrial locks with the positioning rods partially withdrawn.
Figure 13A:
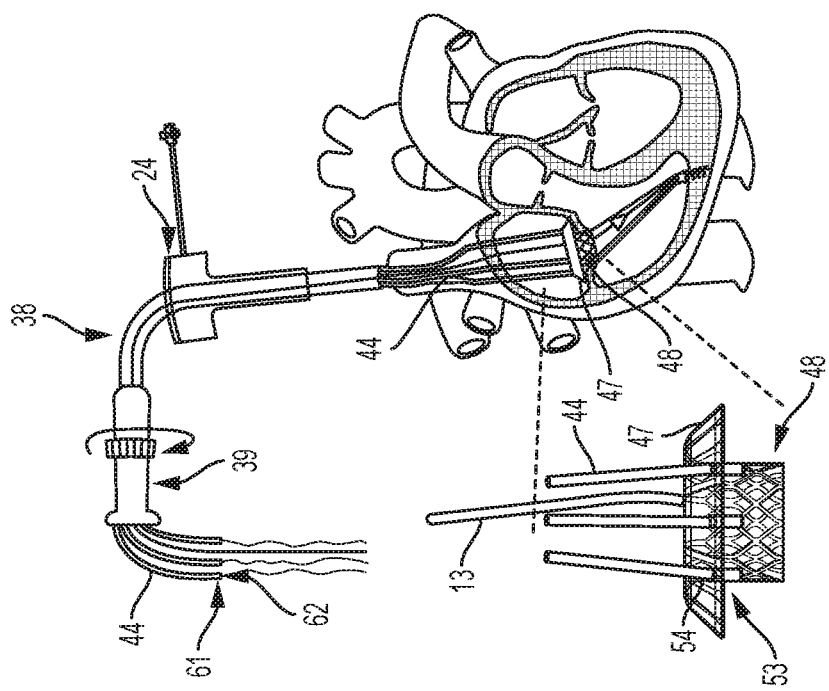
FIG. 13A is a perspective view of the atrial sealing skirt being positioned onto the right atrial floor by the atrial positioning rods.

With reference to FIGS. 13A and 13B, the at least one atrial positioning rod 44 has a distal end 54, a proximal end 61 and an inner rod lumen 62 extending there between, the inner rod lumen being sized and configured so that a portion of a suture 45 and/or a cord 21 is inserted therethrough. At least a portion of the atrial positioning rod 44 is flexible so that the distal end 54 of the atrial positioning rod may be positioned at or adjacent to the deployment site 5.

Figure 17A:
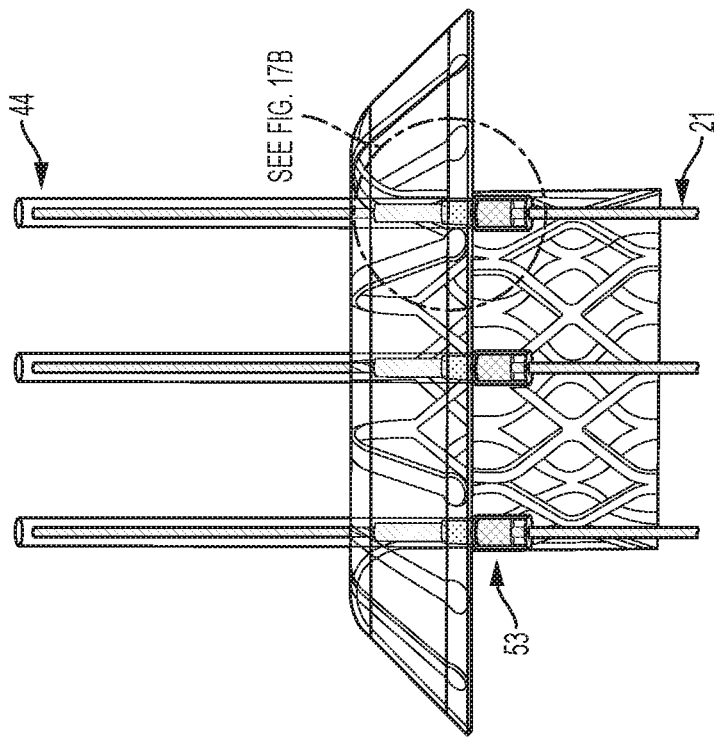
FIG. 17A is an enlarged side elevational view of the atrial sealing skirt coupled to atrial positioning rods and cords.

The at least one positioning rod 44 is coupled to the conduit 53. As illustrated FIGS. 13A and 13B, each conduit 53 contains a detachable lock 56 (FIGS. 17A and 17B), which is configured to securely attach at least one cord 21. Thus, the cord 21 is securely attached to the tether rod 19 of the tether 18, which is coupled to anchor cap 16, secured to intracardiac wall 7 via the anchor screw 17, and the detachable lock 56 securely attaches the cord 21 in the right atrium, for example.

Figure 21B:
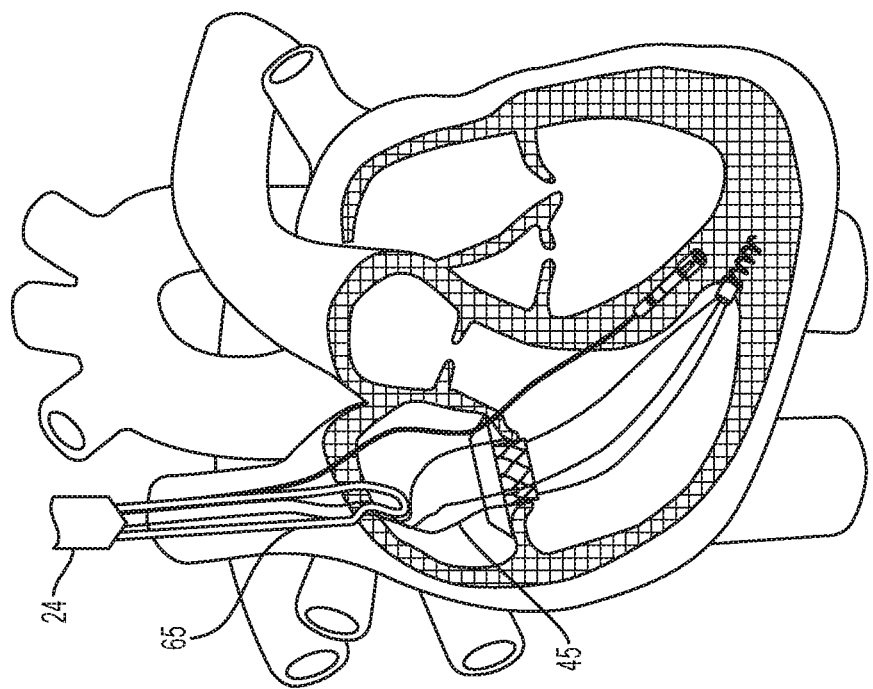
FIG. 21B is a cut away view of a heart with the atrial skirt positioned within the heart and illustrating the suture cutter.

Referring to FIGS. 17A, 17B, 18A, 18B, 19A and 19B, the locking system 55 consists of a detachable lock 56, integrated inside conduit 53, attached to first gateway hypotube 57 and second retracting hypotube 58. Inside the detachable lock 56 is a locking clip 59. With reference now to FIG. 21B, the system 1 further comprises a suture cutter 65 sized and configured to pass through the delivery sheath 24 to cut the at least one suture 45 (as shown in FIG. 21B).

The Method of Implanting, Positioning and Locking the Atrial Skirt

In use, the system 1 implants the atrial sealing skirt 46 (with an integrated valve) utilizing a transcatheter approach by placing a right or left ventricular anchor 75 and docking a tether 18 to the anchor 75. As shown in FIG. 12A, the atrial sealing skirt delivery system 37 is inserted over the flexible wire 13 of the delivery cable 12 and into a portion of the heart 2. As the atrial sealing skirt delivery guide 38, with the atrial sealing skirt 46 and integrated valve 100 preloaded into distal end 41, is inserted into the heart, at least a portion of the suture 45 is threaded through the at least one conduit 53 defined in the wall of the atrial sealing skirt 46, illustrated in FIGS. 12B and 12C, and as atrial sealing skirt delivery guide 38 advances, at least a portion of suture 45 and cord 21 extend along and proximally beyond the inner guide lumen 40 of the atrial sealing skirt delivery guide 38. Thus, a portion of the at least one cord 21 extends through and beyond the distal end 41 of the atrial sealing skirt delivery guide 38, and a portion of the at least one suture 45 extends through and beyond the atrial sealing skirt delivery guide 38. The atrial sealing skirt delivery guide 38 is positioned so that the distal end 41 of the atrial sealing skirt delivery guide 38, with the atrial sealing skirt 46 and valve 100 preloaded into distal end 41, is passed through the deployment site 5 and into the right ventricle 6.

The atrial sealing skirt 46 and valve 100 are preloaded into distal end 41 of the atrial sealing skirt delivery guide 38 for positioning at the deployment site 5. As shown, the suture 45 is pre-assembled with the valve 100 such that each suture 45 is threaded through the at least one conduit 53 defined in the wall of the atrial sealing skirt 46, illustrated in FIGS. 12B and 12C. As the atrial sealing skirt 46 and distal end 41 of atrial sealing skirt delivery guide 38 advance as a unit and approach the deployment site, the end of the suture 45 and a portion of the cord 21 will become threaded through the conduit 53 defined in the atrial sealing skirt 46. As such, the atrial sealing skirt 46 is moveable along the length of the at least one cord until the desired deployment site 5 has been reached. That is, the atrial sealing skirt is free floating on the cord 21 until locked in placed by the detachable lock 56.

When the atrial sealing skirt 46 is in the desired deployment site 5, the atrial sealing skirt deployment knob 39 is utilized to at least partially withdraw the delivery guide 38 around the atrial sealing skirt 46. With the guide 38 free of the sealing skirt 46, the skirt 46 expands to its full, unrestrained size. Optionally, because the atrial sealing skirt's position is adjustable, the atrial sealing skirt deployment knob 39 is used to expand the sealing skirt 46 near the desired deployment site.

An atrial positioning rod 44 is then be inserted over each suture 45 such that a portion of each suture 45 extends within inner rod lumen 62 and a portion of each suture extends beyond the proximal end 61 of the positioning rod 44. With reference to FIGS. 13A and 13B, the positioning rod 44 is then inserted through atrial sealing skirt guide 38 and a portion of the cord 21 is received by the inner rod lumen 62 of the rod 44 and the distal end 54 of the positioning rod (with the detachable lock 56 attached thereto) is adjacent to the atrial sealing skirt 46. The positioning rods 44 are pushed down by the user until the sealing skirt is in a desired position relative to the tricuspid annulus.

The atrial sealing skirt 46 position does not require pulling a tether 18 through the ventricular apex heart 2, because the atrial sealing skirt 46 moves freely over the tether 18 until the desired skirt 46 position is achieved. After the desired valve position is achieved, the at least one atrial positioning rod 44 urges the atrial sealing skirt 46 into position and is locked into place via a detachable lock 56 nestled within each conduit 53 and connected to the end of each positioning rod 44. The atrial sealing skirt 46 may be repositioned or retrieved until release of the sutures 45 that extend through each atrial positioning rod 44

Figure 15B:
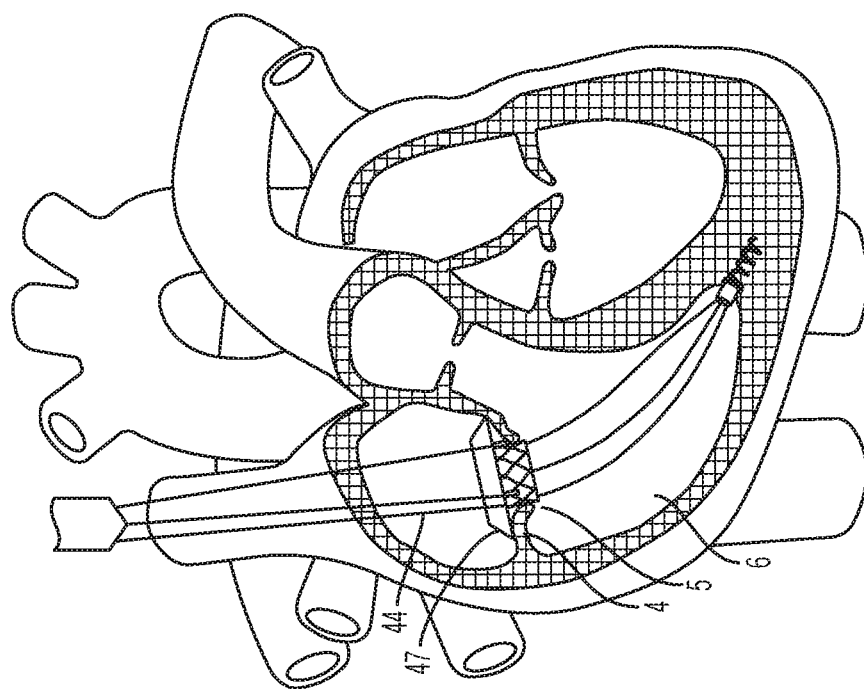
FIG. 15B is a cut-away perspective view of the heart showing the atrial sealing skirt positioned onto, and conforming to, the atrial floor.
Figure 15A:
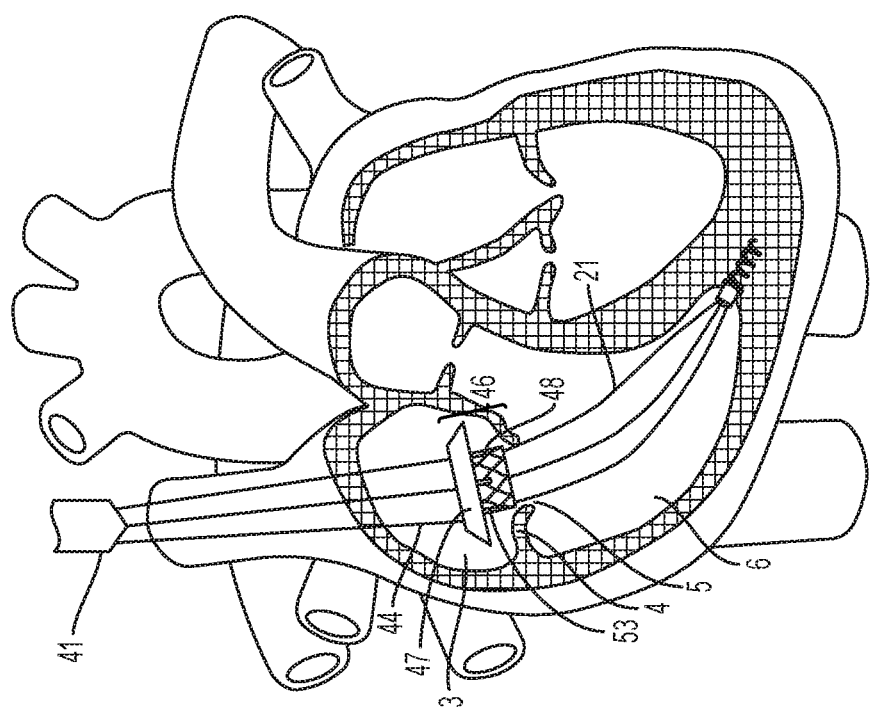
FIG. 15A is a cut-away perspective view of the heart showing the atrial sealing skirt being positioned.

As shown in FIGS. 15A and 15B, the positioning of the atrial sealing skirt 46 inside the right atrium 3 so that the atrial skirt top brim 47 conforms to the topography of the right atrial floor 4 is shown. Via the atrial sealing skirt delivery system end 41, the practitioner advances one or more atrial positioning rods 44 so that the atrial sealing skirt 46 translates over one or more cords 21, which extend through one or more conduits 53, defined by the atrial skirt body 48. As shown in FIG. 15B, as the atrial sealing skirt 46 advances toward the right ventricle 6, the atrial skirt top brim 47 contacts the atrial floor 4, and the one or more extension members 49 flex differentially according to the local anatomy. Because each atrial positioning rod 44 is pushed with differential force, precise tension amounts are achievable, and therefore more or less flexion of the extensions members 49 to facilitate conformation of the atrial skirt top brim 47 around the entire perimeter of the atrial floor 4 to limit regurgitation through the tricuspid valve orifice.

Figure 22:
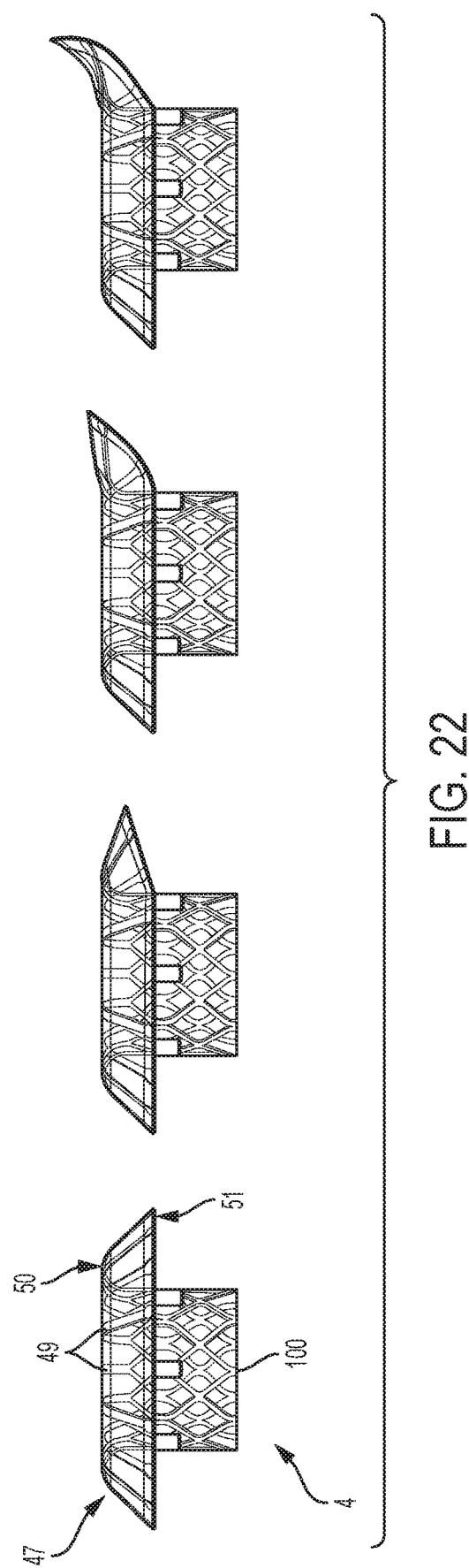
FIG. 22 is a side elevational view of the sealing skirt with one edge transitioning from a concave to a convex configuration.

FIG. 22 illustrates the conversion of the atrial skirt top brim 47 from concave to convex. As the valve is pushed down to the atrial floor 4 by atrial positioning rod 44 (FIGS. 15A and 15B), which is attached to the extension member base 50 of the extension member 49, the extension member tip 51 flexes upward, conforming to the convex atrial floor anatomy. Further distal movement of the valve 100 (shown left to right in FIG. 22) further modifies the shape of the sealing skirt 46 as it confirms to the atrial floor and as the extension member base 50 are urged downward by atrial positioning rod 44 (FIGS. 13A, 15A and 15B). By way of example only, the description of positioning and conforming of the atrial sealing skirt 46, as described above, refers to positioning of the atrial sealing skirt 46 onto the left atrial floor 9, thereby limiting regurgitation through the mitral valve orifice 10.

Now referring to FIGS. 19A and 19B, pulling of the retracting hypotube 58 causes retraction of locking clip 59, which pushes down on locking tabs 63, engaging cord 21. More specifically, the second hypotube 58 is retracted and due to its connection to the locking clip 59, it also retracts the locking clip 59. The locking clip 59, upon retraction, contacts the contact points 64 of the first gateway hypotube 57, disconnecting the clip 59 permitting the second hypotube 58 to be removed. Once retracting hypotube 58 is pulled, the inner arms of gateway hypotube 57 spring inward, allowing gateway hypotube to be removed. The first gateway hypotube 57 is beneficial as it enables the cord 21 to be locked while the second hypotube 58 is being retracted. The gateway hypotube 57 is then removed, leaving the clip 59 within the conduit 53 of the atrial sealing skirt 46. FIG. 20A shows a cut-away view of a lock fully engaged. According to one aspect, the positioning rod 44 may be integrated with the gateway hypotube or removably connected thereto. FIG. 20B shows an intact view of a fully engaged lock. It is to be appreciated that the locking system of Applicants' application Ser. No. 15/943,792 may be employed in place of the locking system described herein. The locking systems may be employed in either system without departing from the spirit and scope of the present invention.

Figure 21A:
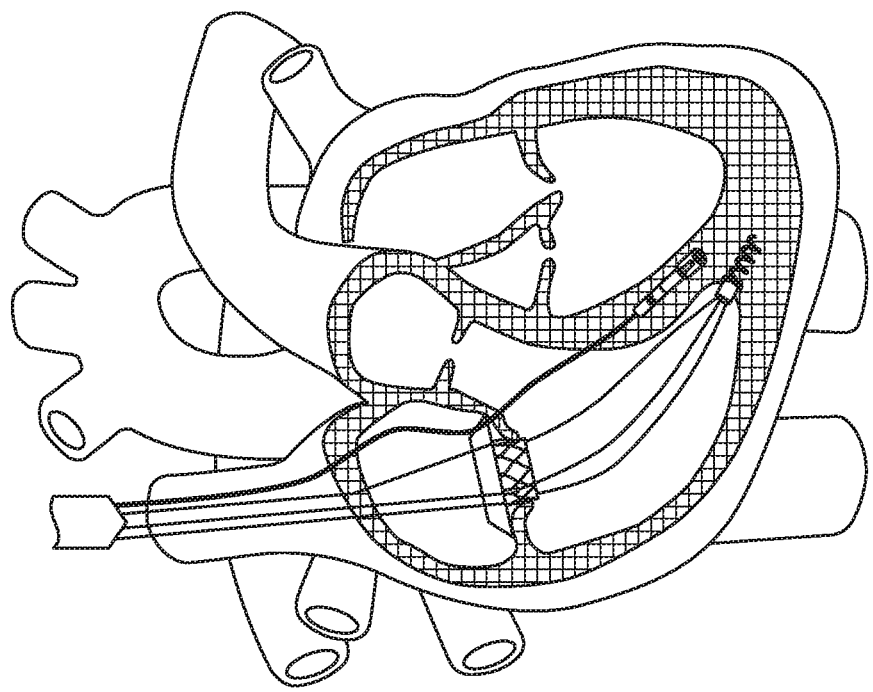
FIG. 21A is a cut away view of a heart with the atrial skirt positioned within the heart and all delivery devices removed.

As illustrated in FIGS. 21A and 21B, with the atrial sealing skirt securely conforming to atrial floor 4, the suture cutter 65 is advanced over the sutures 45 and to the atrial skirt top brim 47. The suture cutter 65 cuts and releases the distal end of each suture 45 above the detachable lock 56. The sutures 45 and the suture cutter 65 are then be removed from the heart 2

In one aspect, prior to cutting of the sutures 45, the atrial sealing skirt 46 may be retrieved or repositioned. For example, if it is determined that the atrial sealing skirt is to be removed or repositioned, an atrial positioning rod 44 is positioned over each suture so that a portion of the suture is in the inner rod lumen 62. When the distal end 54 of the positioning rod is adjacent to or in contract with the detachable lock 56, advancing the gateway hypotube 57 and the retracting hypotube 58 attaches the detachable lock to the distal end of the positioning rod, thereby unlocking the lock from the cord 21. With each cord unlocked, the valve may be removed from and/or repositioned in the deployment site 5.

In another aspect, the atrial sealing skirt 46 may be repositioned and/or removed days to weeks after valve deployment. In this aspect, the sutures are not cut, but wrapped around a spool or other wrapping device. This device is then attached to the valve on the atrial skirt top brim 47. Days after deployment of the valve and completion of the procedure, the spool/wrapping device may be re-captured, allowing un-wrapping and retrieval of the sutures. An atrial positioning rod 44 is then positioned over each suture so that a portion of the suture is in the inner rod lumen 62. When the distal end 54 of the positioning rod is adjacent to or in contract with the detachable lock 56, advancing the gateway hypotube 57 and the retracting hypotube 58 attaches the detachable lock to the distal end of the positioning rod, thereby unlocking the lock from the cord 21. With each cord unlocked, the valve is removed from and/or repositioned in the deployment site 5.

Although several aspects of the invention have been disclosed in the foregoing specification, it is understood by those skilled in the art that many modifications and other aspects of the invention will come to mind to which the invention pertains, having the benefit of the teaching presented in the foregoing description and associated drawings. It is thus understood that the invention is not limited to the specific aspects disclosed hereinabove, and that many modifications and other aspects are intended to be included within the scope of the appended claims. Moreover, although specific terms are employed herein, as well as in the claims that follow, they are used only in a generic and descriptive sense, and not for the purposes of limiting the described invention.

What is claimed is:

1. A medical assembly for minimally invasively implanting an atrial sealing skirt in the heart at an atrial sealing skirt deployment site comprising:
   an atrial sealing skirt configured for receiving a valve and for endovascular introduction and implantation at a deployment site and configured and sized to replace a native heart valve, said atrial sealing skirt having a portion being configured to substantially conform to an atrial floor adjacent the valve deployment site;
   an anchor assembly configured and sized for endovascular introduction for implanting an anchor to an intracardiac wall at an implantation site and comprising a delivery cable;
   a tether advanced over said delivery cable and includes at least one cord connected to said anchor and said atrial sealing skirt for operatively connecting said atrial sealing skirt and said anchor;
   a removable anchor delivery system for introducing said anchor endovascularly; and
   a removable atrial sealing skirt delivery system for positioning and sealing the atrial sealing skirt.

2. The medical assembly according to claim 1 wherein said anchor assembly comprises:
   an anchor cap having a proximal and distal end;
   an anchor screw extending from the anchor cap distal end and configured for penetration a predetermined distance into the intracardiac wall at the implantation site; and
   at least one lock on said anchor cap for locking said tether, said lock being selectively moved from a first locked position to a second unlocked position.

3. The medical assembly according to claim 2 wherein said at least one lock is a locking arm extending radially outwardly from said anchor cap.

4. The medical assembly according to claim 2 wherein said anchor comprises at least two of said locks.

5. The medical assembly according to claim 2 wherein said anchor delivery assembly comprises:
   an anchor delivery guide defining a longitudinally extending lumen and having a proximal and distal end;
   an anchor delivery rod defining a longitudinally extending lumen and having a proximal and distal end and having a distal portion wherein side walls of said delivery rod lumen have a second configuration and wherein a proximal portion of said-anchor cap includes a first configuration for cooperating with said delivery rod lumen second configuration for selectively mating therewith for implantation of said anchor screw at the implantation site.

6. The medical assembly according to claim 5 wherein said anchor delivery assembly further comprises a sheath defining a longitudinally extending lumen for receiving a portion of said anchor delivery guide, said sheath having a length less than the length of the said anchor delivery guide defined between said proximal and distal ends.

7. The medical assembly according to claim 6 further comprising a guide handle for receiving a proximal portion of said anchor delivery sheath.

8. The medical assembly according to claim 5 wherein said anchor delivery system further comprises a rotating handle on a proximal end of said delivery rod for facilitating rotation of said delivery rod to rotate said anchor.

9. The medical assembly according to claim 1 wherein said atrial anchor assembly further comprises:
   an anchor cap having a proximal and distal end wherein said proximal end includes a first surface configuration;
   an anchor screw extending from the anchor cap distal end and configured for penetration a predetermined distance into the intracardiac wall at the implantation site; and
   said delivery cable comprises a distal end having a second surface configuration configured to mate with said anchor cap proximal end surface configuration.

10. The medical assembly according to claim 9 wherein said delivery cable comprises a flexible wire.

11. The medical assembly according to claim 9 wherein said anchor cap first surface configuration is defined by a cavity having threaded sidewalls and said second configuration of said delivery cable distal end is an outer surface configuration which is threaded to mate and engage said anchor cap wherein said anchor delivery cap rotates said anchor cap when rotational forces are applied thereto.

12. The medical assembly according to claim 9 wherein said tether comprises:
   a docking ring defining a central aperture for receiving at least a portion of the delivery cable; and
   at least one tether rod moveably connected to said docking ring.

13. The medical assembly according to claim 12 wherein said anchor cap comprises at least one lock, said lock being selectively moved from a first locked position to a second unlocked position and said tether docking ring cooperates with said at least one lock of the anchor cap for securing the tether on the anchor cap when said lock is in said first position.

14. The medical assembly according to claim 13 wherein said at least one tether rod is rotatably connected to said docking ring and is substantially rigid.

15. The medical assembly according to claim 14 wherein a distal end of said tether rod defines a hook and said docking ring includes an eyelet configured for receipt of said hook.

16. The medical assembly according to claim 12 wherein said tether further includes at least one suture extending from a proximal end of said at least one tether rod.

17. The medical assembly according to claim 16 wherein said tether comprises at least two of said tether rods and each of said at least two of said sutures extending from a respective one of said tether rods.

18. The medical assembly according to claim 1 further comprising a J-wire configured for endovascular insertion to guide said anchor delivery system.

19. The medical assembly according to claim 1, said tether further comprising at least one suture extending from a proximal end of said at least one cord.

20. The medical assembly according to claim 1 further comprising a tether delivery assembly comprising a removeable tether delivery sheath defining a longitudinally extending lumen configured for receipt of said tether.

21. The medical assembly according to claim 1 wherein said atrial skirt delivery system comprises:
   an atrial sealing skirt delivery guide having proximal and distal ends and defining an inner guide extending lumen therebetween wherein a delivery sheath is removable and positioned along said delivery cable and wherein said sheath includes said atrial sealing skirt operatively connected to said cord which extends within a lumen of said sheath.

22. The medical assembly according to claim 21 wherein said tether comprises a docking ring defining a central aperture for receiving the flexible wire of the delivery cable and at least one tether rod moveably connected to said docking ring and said delivery guide also includes said tether within said lumen wherein said atrial sealing skirt is connected to said tether within said lumen.

23. The medical assembly according to claim 22 wherein said atrial skirt delivery system further comprises an atrial sealing skirt deployment knob having a central channel for receiving a proximal portion of said atrial sealing skirt delivery guide and wherein said atrial sealing skirt delivery guide is retractable within said atrial sealing skirt deployment knob when retracted.

24. The medical assembly according to claim 23 wherein said atrial skirt delivery system further comprises at least one positioning rod having a central lumen for being inserted over said at least one cord of said tether and wherein said at least one positioning rod has a length sufficient to extend proximal to said deployment knob and into the heart so as to contact said atrial sealing skirt.

25. The medical assembly according to claim 1 further comprising a locking system for locking said atrial sealing skirt positioned on the atrial floor and wherein said atrial skirt delivery system further comprises at least one positioning rod having a central lumen for being inserted over said at least one cord of said tether, said atrial sealing skirt comprising an atrial top brim, and said locking system comprises at least one conduit extending below said top brim and wherein said top brim defines at least one aperture of said conduit and said locking system further comprises a detachable lock positioned within said conduit configured to cooperate with said at least one positioning rod to lock said top brim on the atrial floor.

26. The medical assembly according to claim 25 wherein said detachable lock defines a central lumen and said cord of said tether is received within said lock lumen.

27. The medical assembly according to claim 26 wherein said locking system further comprises a first gateway hypotube defining a central lumen and configured for receipt by said detachable lock lumen and configured to cooperate with said detachable lock to secure said at least one cord.

28. The medical assembly according to claim 1 wherein said atrial sealing skirt defines a valve receptacle and said medical assembly comprises a valve within said valve receptacle.

* * * * *